(12) United States Patent
Shyamala

(10) Patent No.: US 7,132,233 B2
(45) Date of Patent: Nov. 7, 2006

(54) IDENTIFICATION OF OLIGONUCLEOTIDES FOR THE CAPTURE, DETECTION AND QUANTITATION OF WEST NILE VIRUS

(75) Inventor: Venkatakrishna Shyamala, Oakland, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

(21) Appl. No.: 10/729,421

(22) Filed: Dec. 5, 2003

(65) Prior Publication Data

US 2005/0032729 A1 Feb. 10, 2005

Related U.S. Application Data

(60) Provisional application No. 60/480,431, filed on Jun. 20, 2003, provisional application No. 60/432,580, filed on Dec. 12, 2002.

(51) Int. Cl.
*C12Q 1/70* (2006.01)
*C12Q 1/68* (2006.01)
*C07H 21/00* (2006.01)
*C12N 7/00* (2006.01)

(52) U.S. Cl. .......................... 435/5; 435/6; 435/235.1; 536/25.6

(58) Field of Classification Search .................... 435/4, 435/5, 6, 239, 7.1; 536/224.1
See application file for complete search history.

(56) References Cited

U.S. PATENT DOCUMENTS 5,939,254 A 8/1999 Ennis

FOREIGN PATENT DOCUMENTS

| WO | WO 2004/036190 | 4/2004 |
| WO | WO 2004/092412 | 10/2004 |

OTHER PUBLICATIONS

Bhatt et al., "Detection of Nucleic Acids by Cycling Probe Technology on Magnetic Particles; High Sensitivity and Ease of Separation," Nucleosides Nucleotides, 18(6-7): 1297-9 (1999).*
Buck et al., "Design strategies and performance of custom DNA sequencing primers" (Biotechniques (1999) 27(3):528-536).*
King et al. ("Development of a Taqman PCR assay with internal amplification control for the detection of African swine fever virus," Journal of Virological Methods, 107: 53-61 (2003)☐☐.*

Suzuki et al. ("Poly A-linked non-isotopic microtiter plate reverse transcriptase assay for detection of clinical human immunodeficiency virus isolates," Journal of Virological Methods, 55: 347-356 (1995)).*
Shyamala et al., "Performance Characteristics of the Validated and Improved Qualitative and Quantitative Target-Capture PCR WNV NAT Assays," Scientific Section, Transfusion, vol. 44, Supplement (2004) SP377.
Busch et al., "West Nile Virus RNA Dynamics and Antibody Evolution Based on Follow-Up of Viremic Blood Donors," Scientific Section, Transfusion, vol. 44, Supplement (2004) P6-030A.
Cline et al., "Gen-Probe Alternative WNV Assay: A TMA-Based Confirmatory Assay for West Nile Virus," Scientific Section, Transfusion, vol. 44, Supplement (2004) SP368.
Anderson et al., "Isolation of West Nile Virus From Mosquitoes, Crows, and a Cooper's Hawk in Connecticut", *Science* (1999) 286: 2331-2333.
Berthet et al., "Extensive Nucleotide Changes and Deletions Within the Envelope Glycoprotein Gene of Euro-African West Nile Viruses", *J. of General Virol.* (1997) 78: 2293-2297.
Briese et al., "Detection of West Nile Virus Sequences in Cerebrospinal Fluid" ,*The Lancet* (2000) 355: 1614-1615.
Brinton, "The Molecular Biology of West Nile Virus: A New Invader of the Western Hemisphere" , *Ann. Rev. Microbiol* (2002), 56: 371-402.
Burt et al., "Phylogenetic Relationships of Southern African West Nile Virus Isolates", *Emerging Infectious Diseases* (2002) 8 (8): 820-826.
Lanciotti et al., "Origin of the West Nile Virus Responsible for an Outbreak of Encephalitis in the Northeastern United States", *Science* (1999), 286: 2333-2337.
Lanciotti et al., "Rapid Detection of West Nile Virus From Human Clinical Specimens, Field-Collected Mosquitoes, and Avian Samples by a Taqman Reverse Transcriptase-PCR Assay", *J. Clin. Microbiol.* (2000) 38: 4066-4071.
Lanciotti et al., "Nucleic Acid Sequence-Based Amplification Assays for Rapid Detection of West Nile and St. Louis Encephalitis Viruses",*J. Clin. Microbiol.* (2001) 39: 4506-4513.
Chin, Andrew, CD-ROM document, entitled "On the Preparation and Utilization of Isolated and Purified Oligonucleotides," including copy of letter, dated Feb. 17, 2005 from Andrew Chin.

* cited by examiner

*Primary Examiner*—Bruce R. Campell
*Assistant Examiner*—M. Franco Salvoza
(74) *Attorney, Agent, or Firm*—Marcella Lillis; Roberts L. Robins; Alisa A. Harbin

(57) ABSTRACT

West Nile virus capture oligonucleotides, primers and probes derived from conserved regions of the West Nile virus genome are disclosed. Also disclosed are nucleic acid-based assays using the capture oligonucleotides, primers and probes.

18 Claims, 3 Drawing Sheets

| | | |
|---|---|---|
| (A) | VWNVC1 - gcacatgtatcccacatccattg | (SEQ ID NO: 1) |
| (B) | VWNVC2 - ctctgacaatgcataggttcttt | (SEQ ID NO: 2) |
| (C) | VWNVC3 - ccagcagctgttggaatcgtg | (SEQ ID NO: 3) |
| (D) | VWNVC4 - tgacatctgtgacgtcagtagc | (SEQ ID NO: 4) |
| (E) | VWNVC5 - tttaccgtcatcatcaccttccc | (SEQ ID NO: 5) |
| (F) | VWNVC6 - ttggaagttagagagggtaactg | (SEQ ID NO: 6) |
| (G) | VWNVC7 - ctcctacgctggcgatcaggcc | (SEQ ID NO: 7) |
| (H) | VWNVC8 - tcatgactgcaattccggtcttt | (SEQ ID NO: 8) |
| (I) | VWNVC9 - gagctccgccgattgatagca | (SEQ ID NO: 9) |
| (J) | VWNVC10 - ctggtcaaggtccctagttcc | (SEQ ID NO: 10) |
| (K) | VWNVC11 - ttcttaaaactcagaaggtgtttca | (SEQ ID NO: 11) |
| (L) | VWNVC12 - tcgctgtttgtttgttcacacctc | (SEQ ID NO: 12) |
| (M) | VWNVC13 - tccatcgatccagcactgctcgggtc | (SEQ ID NO: 13) |
| (N) | VWNVC14 - ggagcaattgctgtgaacctgaa | (SEQ ID NO: 14) |
| (O) | VWNVC15 - gaacgccaagagagccaacac | (SEQ ID NO: 15) |
| (P) | VWNVC16 - tcgtattggccccttgccgtcg | (SEQ ID NO: 16) |
| (Q) | VWNVC45 - gtccacctcttgcgaaggac | (SEQ ID NO: 45) |
| (R) | VWNVC46 - ctgtgccgtgtggctggttgt | (SEQ ID NO: 46) |
| (S) | VWNVC18 - cctagtctatcccaggtgtc | (SEQ ID NO: 50) |

FIGURE 1

```
agtagttcgcctgtgtgagctgacaaacttagtagtgtttgtgaggatta   50
acaacaattaacacagtgcgagctgtttcttagcacgaagatctcgatgt  100
ctaagaaaccaggagggcccggcaagagccgggctgtcaatatgctaaaa  150
cgCAGTGACATGCAGGTCTAGCTtccttgattggactgaagagggctatg  200
ttgagcctgatcgacggcaaggggccaatacgatttgtgttggctctctt  250
ggcgttcttcaggttcacagcaattgctccgacccgagcagtgctggatc  300
gatggagaggtgtgaacaaacaaacagcgatgaaacaccttctgagtttt  350
aagaaggaactagggaccttgaccagtgctatcaatcggcggagctcaaa  400
acaaaagaaaagaggaggaaagaccggaattgcagtcatgattggcctga  450
tcgccagcgtaggagcagttaccctctctaacttccaagggaaggtgatg  500
atgacggtaaatgctactgacgtcacagatgtcatcacgattccaacagc  550
tgctggaaagaacctatgcattgtcagagcaatggatgtgggatacatgt  600
gcgatgatactatcacttatgaatgcccagtgctgtcggctggtaatgat  650
ccagaagacatcgactgttggtgcacaaagtcagcagtctacgtcaggta  700
tggaagatgcaccaagacacgccactcaagacgcagtcggaggtcactga  750
cagtgcagacacacggagaaagcactctagcgaacaagaaggggcttgg   800
atggacagcaccaaggccacaaggtatttggtaaaaacagaatcatggat  850
cttgaggaaccctggatatgccctggtggcagccgtcattggttggatgc  900
ttgggagcaacaccatgcagagagttgtgtttgtcgtgctattgcttttg  950
gtggccccagcttacag                                   967
```

FIGURE 2

(A)     cggaatgccccgcgtgttg         (SEQ ID NO: 52)
(B)     cggtatgccccgcggattg         (SEQ ID NO: 53)
(C)     tctgcggagagtgcagtctgcgat    (SEQ ID NO: 54)
(D)     tgcacgctgacactgggtgtgc      (SEQ ID NO: 55)

FIGURE 3

IDENTIFICATION OF OLIGONUCLEOTIDES FOR THE CAPTURE, DETECTION AND QUANTITATION OF WEST NILE VIRUS

CROSS-REFERENCE TO RELATED APPLICATIONS

This application is related to U.S. application Ser. No. 60/432,850, filed Dec. 12, 2002, and Ser. No. 60/480,431, filed Jun. 20, 2003, from which applications priority is claimed under 35 USC § 119(e)(1) and which applications are incorporated herein by reference in their entireties.

TECHNICAL FIELD

The present invention pertains generally to viral diagnostics. In particular, the invention relates to nucleic acid-based assays for accurately diagnosing West Nile virus infection and detecting the presence of West Nile virus in a biological sample.

BACKGROUND OF THE INVENTION

West Nile virus (WNV) is a mosquito-borne flavivirus that infects humans, horses, and birds. The virus is transmitted to humans and several animal species through mosquitoes that acquire the virus by feeding on infected birds. The virus is indigenous to Africa, Asia, Europe, and Australia, and has recently caused large epidemics in the Western Hemisphere, including in Europe and the United States. WNV was first detected in North America in 1999 during an epidemic of meningoencephalitis in New York City. WNV seroprevalence studies in Queens, N.Y. showed evidence of prior infection in 2.6% of the population, age 5 or older. During 1999–2002, the virus extended its range throughout much of the eastern United States. The range of WNV infections within the Western Hemisphere is expected to continue to expand.

Human WNV infections are often subclinical but clinical infections can range in severity from uncomplicated fever to fatal meningoencephalitis. The incidence of severe neuroinvasive disease and death increases with age. Epidemics of WNV encephalitis and meningitis raise concerns that transmission of WNV may occur through voluntary blood donations. As with other flaviviruses, WNV possesses a single-stranded plus-sense RNA genome of approximately 11,000 nucleotides. The genome contains a single open reading frame (ORF) of about 10,300 nucleotides that encodes a polyprotein that is proteolytically processed into 10 mature viral proteins, in the order of $NH_2$—C-prM-E-NS1-NS2A-NS2B-NS3-NS4A-NS4B-NS5-COOH. The three structural proteins, capsid (C), membrane (prM), and envelope (E), are encoded within the 5' portion of the ORF, while the seven nonstructural proteins, NS1, NS2A, NS2B, NS3, NS4A, NS4B and NS5, are encoded within the 3' portion. The boundaries of these proteins, numbered relative to the nucleotide sequence of WNV, strain EG101, are as follows: C, 97–465; pr, 466–741; M, 742–986; E, 987–2469; NS1, 2470–3525; NS2A, 3526–4218; NS2B, 4219–4611; NS3, 4612–6458; NS4A, 6459–6915; NS4B, 6916–7680; NS5, 7681–10395. For a review of WNV and its molecular structure, see, Brinton, M. A., *Ann. Rev. Micorbiol.* (2002) 56:371–402; and Lanciotti et al., *Science* (1999) 286:2333–2337.

To date, no effective prevention or treatment of WNV infection exists. Currently, then, public education and mosquito abatement programs are used to curb transmission of the virus. However, rapid intervention is critical in order to reduce the risk to humans. Traditionally, detection of virus has been accomplished by testing mosquitoes and dead birds for the presence of virus using cell culture methods and immunoassay techniques. However, these methods are extremely time consuming and can take a week or more to complete.

The diagnosis of WNV infection in humans can be established by the presence of WNV IgM antibody in serum or cerebrospinal fluid (CSF), increases in WNV antibody detected by ELISA or WNV neutralizing antibody. However, confirmation of the type of infecting virus is possible only by detection of a fourfold or greater rise in virus-specific neutralizing antibody titers in either CSF or serum by performing plaque reduction neutralization assays with several flaviviruses. Virus isolation in cell culture from CSF and serum has generally been unsuccessful, likely due to the low level and short-lived viremia associated with infection. Additionally, immunological tests are indirect, and nonspecific antigen-antibody reactions can occur and result in false-positive determinations. Hence, immunological tests have serious drawbacks, limited utility and provide only an indirect index of potential viral infectivity.

Recently, TAQMAN fluorogenic 5' assays have been used to detect WNV in CSF specimens. Briese et al., *The Lancet* (2000) 355:1614–1615; Lanciotti et al., *J. Clin. Microbiol.* (2000) 38:4066–4071. Lanciotti et al., *J. Clin. Microbiol.* (2001) 39:4506–4513 describes the use of nucleic acid sequence-based amplification (NASBA) for detecting WNV. This amplification technique employs three enzymes, reverse transcriptase, T7 RNA polymerase and RNase H and the final amplification product is single-stranded RNA with a polarity opposite of the target. The amplified RNA product can be detected using a target-specific capture probe bound to a substrate, in combination with a labeled detector probe. Alternatively, amplified RNA can be specifically detected in real-time using molecular beacon probes in the amplification reaction.

Nevertheless, there remains a need for the development of reliable and efficient methods of detecting WNV in samples from humans and animals, in order to curb transmission of the virus.

SUMMARY OF THE INVENTION

The present invention is based on the development of a sensitive, reliable nucleic acid-based diagnostic test for the detection of WNV in biological samples, particularly blood samples, from potentially infected subjects. The techniques described herein utilize extracted sample nucleic acid as a template for amplification of conserved genomic regions of the WNV sequence using transcription-mediated amplification (TMA), as well as in a 5' nuclease assay, such as the TAQMAN real-time PCR technique. The methods allow for the detection of as few as 10 copies of the target WNV sequence in viremic samples. Moreover, the methods described herein provide for a one-pot analysis wherein captured sample nucleic acids can be subjected to amplification and detection in the same container. Using the methods of the invention, infected samples can be identified and excluded from the blood supply for transfusion, as well as for the preparation of blood derivatives.

Accordingly, in one embodiment, the invention is directed to an isolated oligonucleotide not more than 60 nucleotides in length comprising:

(a) a nucleotide sequence of at least 10 contiguous nucleotides, preferably at least 15 contiguous nucleotides, more preferably at least 20 contiguous nucleotides, or any number of contiguous nucleotides between 10 and 60, from a sequence selected from the group consisting of SEQ ID NOS: 1–16, 34–39, 42–46, 49 and 50; (b) a nucleotide sequence having 90% sequence identity to a nucleotide sequence of (a); or (c) complements of (a) and (b).

In additional embodiments, the oligonucleotide is selected from the group consisting of SEQ ID NOS:52, 53, 54 and 55 and comprises a detectable label. In certain embodiments, the detectable label is at the 5'-end and/or the 3'-end.

In certain embodiments, the detectable label is a fluorescent label selected from the group consisting of 6-carboxyfluorescein (6-FAM), tetramethyl rhodamine (TAMRA), and 2',4',5',7',-tetrachloro-4-7-dichlorofluorescein (TET). In yet additional embodiments, the oligonucleotide is selected from the group consisting SEQ ID NOS:36, 39, 44 and 45.

In yet another embodiment, the invention is directed to a method for detecting the presence of West Nile virus (WNV) in a biological sample, the method comprising:

isolating nucleic acids from a biological sample suspected of containing WNV;

amplifying the nucleic acids using a sense and an antisense primer wherein each of the primers is not more than about 60 nucleotides in length and is sufficiently complementary to a portion of the sense and antisense strands, respectively, of the isolated nucleic acid to hybridize therewith, and (a) the sense primer comprises SEQ ID NO:34 or a nucleotide sequence having at least 90% sequence identity thereto, or SEQ ID NO:37 or a nucleotide sequence having at least 90% sequence identity thereto, or SEQ ID NO:42 or a nucleotide sequence having at least 90% sequence identity thereto;

(b) the antisense primer comprises SEQ ID NO:35 or a nucleotide sequence having at least 90% sequence identity thereto when the sense primer is SEQ ID NO:34, or the antisense primer comprises SEQ ID NO:38 or a nucleotide sequence having at least 90% sequence identity thereto when the sense primer is SEQ ID NO:37 or the antisense primer comprises SEQ ID NO:43 or a nucleotide sequence having at least 90% sequence identity thereto when the sense primer is SEQ ID NO:42; and detecting the presence of the amplified nucleic acids as an indication of the presence of WNV in the sample.

In additional embodiments, the nucleic acids are isolated from the biological sample by a method comprising:

(a) contacting a solid support comprising capture nucleic acids associated therewith with a biological sample under hybridizing conditions wherein WNV nucleic acid strands, if present in the biological sample, hybridize with the capture nucleic acids; and (b) separating the solid support from the sample.

In certain embodiments, the solid support comprises beads, such as magnetic beads.

In additional embodiments, the isolating, amplifying and detecting are performed in a single container.

In yet further embodiments, the capture nucleic acids comprise one or more oligonucleotides, wherein each of the oligonucleotides is not more than about 60 nucleotides in length and comprises at least 10 contiguous nucleotides from a sequence selected from the group consisting of SEQ ID NOS:1–16, 45, 46 and 50.

In additional embodiments, the capture nucleic acids further comprise a homopolymer chain of about 10–25 nucleotides in length, selected from the group consisting of polyA, polyT, polyG, polyC, and polyU.

In certain embodiments, the amplifying comprises RT-PCR, transcription-mediated amplification (TMA) or TAQ-MAN real-time PCR, or a combination thereof.

In additional embodiments, the amplifying comprises TAQMAN real-time PCR using the sense primer and the antisense primer and detecting is done using at least one probe comprising a detectable label.

In further embodiments, the at least one probe is not more than 60 nucleotides in length and comprises (a) the sequence of SEQ ID NO:52 or the sequence of SEQ ID NO:53 when the sense primer comprises the sequence of SEQ ID NO:34 or (b) the sequence of SEQ ID NO:54 when the sense primer comprises the sequence of SEQ ID NO:37 or (c) the sequence of SEQ ID NO:55 when the sense primer comprises the sequence of SEQ ID NO:42.

In additional embodiments, the method comprises using a probe comprising the sequence of SEQ ID NO:52 and a probe comprising the sequence of SEQ ID NO:53 when the sense primer comprises the sequence of SEQ ID NO:34. The probe may further comprise detectable labels at the 5'-end and at the 3'-end.

In certain embodiments, the detectable label is a fluorescent label selected from the group consisting of 6-carboxyfluorescein (6-FAM), tetramethyl rhodamine (TAMRA), and 2',4',5',7',-tetrachloro-4-7-dichlorofluorescein (TET).

In additional embodiments, an internal control sequence is present. The internal control sequence can comprise the nucleotide sequence of FIG. 2 (SEQ ID NO:17). The method can further comprise a detectably labeled probe sequence for the internal control sequence. In certain embodiments, the detectably labeled probe sequence for the internal control sequence comprises the sequence of SEQ ID NO:40 or SEQ ID NO:41.

In further embodiments, the invention is directed to a kit for detecting the presence of West Nile virus (WNV) in a biological sample, the kit comprising:

capture nucleic acids comprising one or more oligonucleotides, wherein each of the oligonucleotides is not more than about 60 nucleotides in length and comprises a nucleotide sequence of at least 10 contiguous nucleotides of a sequence selected from the group consisting of SEQ ID NOS:1–16, 45 and 46;

primer oligonucleotides wherein the primer oligonucleotides are not more than about 60 nucleotides in length and comprise a nucleotide sequence of at least 10 contiguous nucleotides from SEQ ID NOS:34 and 35 or SEQ ID NOS:37 and 38 or SEQ ID NOS:42 and 43; and written instructions for identifying the presence of WNV.

In additional embodiments, the kit further comprises a polymerase and buffers. In certain embodiments, the kit further comprises at least one probe oligonucleotide of not more than about 60 nucleotides in length and at least 10 contiguous nucleotides, wherein the at least one probe oligonucleotide comprises (a) the sequence of SEQ ID NO:52 or the sequence of SEQ ID NO:53 when the primer oligonucleotides comprise at least 10 contiguous nucleotides from SEQ ID NO:34 and SEQ ID NO:35; or (b) the sequence of SEQ ID NO:54 when the primer oligonucleotides comprise at least 10 contiguous nucleotides from SEQ ID NO:37 and SEQ ID NO:38; or (c) the sequence of SEQ ID NO:55 when the primer oligonucleotides comprise at least 10 contiguous nucleotides from SEQ ID NO:42 and SEQ ID NO:43.

In certain embodiments, the probe further comprises detectable labels at the 5'-end and at the 3'-end. The detectable label can be a fluorescent label selected from the group consisting of 6-carboxyfluorescein (6-FAM), tetramethyl rhodamine (TAMRA), and 2',4',5',7',-tetrachloro-4-7-dichlorofluorescein (TET).

In yet additional embodiments, the kit comprises a probe comprising the sequence of SEQ ID NO:36 and a probe comprising the sequence of SEQ ID NO:49 when the sense primer comprises the sequence of SEQ ID NO:34.

In additional embodiments, the kit further comprises an internal control comprising the nucleotide sequence of FIG. 2 (SEQ ID NO:17).

In further embodiments, the invention is directed to a pair of amplification primers for detecting WNV comprising a pair of oligonucleotides selected from the group consisting of the SEQ ID NO:34/SEQ ID NO:35 pair, the SEQ ID NO:37/SEQ ID NO:38 pair and the SEQ ID NO:42/SEQ ID NO:43 pair.

In additional embodiments, the invention is directed to a set of oligonucleotides for specifically capturing WNV nucleic acid comprising an oligonucleotide of no more than 60 nucleotides in length and comprising the sequence SEQ ID NO:8, an oligonucleotide of no more than 60 nucleotides in length and comprising the sequence SEQ ID NO:12, an oligonucleotide of no more than 60 nucleotides in length and comprising the sequence SEQ ID NO:45, and an oligonucleotide of no more than 60 nucleotides in length and comprising the sequence SEQ ID NO:46.

In another embodiment, the invention is directed to a method of preparing a blood supply comprising whole blood, plasma or serum, substantially free of WNV. The method comprises:

(a) screening aliquots of whole blood, plasma or serum from collected blood samples by any of the detection methods described above;

(b) eliminating samples where WNV is detected; and (c) combining samples where WNV is not detected to provide a blood supply substantially free of WNV.

These and other aspects of the present invention will become evident upon reference to the following detailed description and attached drawings. In addition, various references are set forth herein which describe in more detail certain procedures or compositions, and are therefore incorporated by reference in their entirety.

BRIEF DESCRIPTION OF THE DRAWINGS

FIGS. 1A–1S (SEQ ID NOS:1–16, 45, 46 and 50, respectively) depict exemplary capture oligonucleotides (VWNVC1–VWNVC16, VWNVC45, VWNVC46 and VWNVC18) for isolating WNV RNA from a biological sample.

FIG. 2 (SEQ ID NO:17) depicts an exemplary internal control sequence for use as a control for target capture and amplification. The bolded capitalized letters represent the sequence in the IC that replace the sequence in the target.

FIGS. 3A–3D (SEQ ID NOS:52–55, respectively) show representative probe oligonucleotides for use with the subject methods.

DETAILED DESCRIPTION OF THE INVENTION

The practice of the present invention will employ, unless otherwise indicated, conventional methods of chemistry, biochemistry, recombinant DNA techniques and virology, within the skill of the art. Such techniques are explained fully in the literature. See, e.g., *Fundamental Virology*, 2nd Edition, vol. I & II (B. N. Fields and D. M. Knipe, eds.); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Oligonucleotide Synthesis* (N. Gait, ed., 1984); *A Practical Guide to Molecular Cloning* (1984).

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "an oligonucleotide" includes a mixture of two or more oligonucleotides, and the like.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

I. Definitions

In describing the present invention, the following terms will be employed, and are intended to be defined as indicated below.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. These terms refer only to the primary structure of the molecule. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. In particular, DNA is deoxyribonucleic acid.

A polynucleotide "derived from" or "specific for" a designated sequence refers to a polynucleotide sequence which comprises a contiguous sequence of approximately at least about 6 nucleotides, preferably at least about 8 nucleotides, more preferably at least about 10–12 nucleotides, and even more preferably at least about 15–20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

"Homology" refers to the percent similarity between two polynucleotide or two polypeptide moieties. Two polynucleotide, or two polypeptide sequences are "substantially homologous" to each other when the sequences exhibit at least about 50%, preferably at least about 75%, more preferably at least about 80%–85%, preferably at least about 90%, and most preferably at least about 95%–98% sequence similarity over a defined length of the molecules. As used herein, substantially homologous also refers to sequences showing complete identity to the specified polynucleotide or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100.

Readily available computer programs can be used to aid in the analysis of homology and identity, such as ALIGN, Dayhoff, M. O. in *Atlas of Protein Sequence and Structure* M. O. Dayhoff ed., 5 Suppl. 3:353–358, National biomedical Research Foundation, Washington, D.C., which adapts the local homology algorithm of Smith and Waterman *Advances in Appl. Math.* 2:482–489, 1981 for peptide analysis. Programs for determining nucleotide sequence homology are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent homology of a particular nucleotide sequence to a reference sequence can be determined using the homology algorithm of Smith and Waterman with a default scoring table and a gap penalty of six nucleotide positions.

Another method of establishing percent homology in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence homology." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: ncbi.nlm.gov/cgi-bin/BLAST.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

A "DNA-dependent DNA polymerase" is an enzyme that synthesizes a complementary DNA copy from a DNA template. Examples are DNA polymerase I from *E. coli* and bacteriophage T7 DNA polymerase. All known DNA-dependent DNA polymerases require a complementary primer to initiate synthesis. Under suitable conditions, a DNA-dependent DNA polymerase may synthesize a complementary DNA copy from an RNA template.

A "DNA-dependent RNA polymerase" or a "transcriptase" is an enzyme that synthesizes multiple RNA copies from a double-stranded or partially-double stranded DNA molecule having a (usually double-stranded) promoter sequence. The RNA molecules ("transcripts") are synthesized in the 5' to 3' direction beginning at a specific position just downstream of the promoter. Examples of transcriptases are the DNA-dependent RNA polymerase from *E. coli* and bacteriophages T7, T3, and SP6.

An "RNA-dependent DNA polymerase" or "reverse transcriptase" is an enzyme that synthesizes a complementary DNA copy from an RNA template. All known reverse transcriptases also have the ability to make a complementary DNA copy from a DNA template; thus, they are both RNA- and DNA-dependent DNA polymerases. A primer is required to initiate synthesis with both RNA and DNA templates.

"RNAse H" is an enzyme that degrades the RNA portion of an RNA:DNA duplex. These enzymes may be endonucleases or exonucleases. Most reverse transcriptase enzymes normally contain an RNAse H activity in addition to their polymerase activity. However, other sources of the RNAse H are available without an associated polymerase activity. The degradation may result in separation of RNA from a RNA:DNA complex. Alternatively, the RNAse H may simply cut the RNA at various locations such that portions of the RNA melt off or permit enzymes to unwind portions of the RNA.

As used herein, the term "target nucleic acid region" or "target nucleic acid" denotes a nucleic acid molecule with a "target sequence" to be amplified. The target nucleic acid may be either single-stranded or double-stranded and may include other sequences besides the target sequence, which may not be amplified. The term "target sequence" refers to the particular nucleotide sequence of the target nucleic acid which is to be amplified. The target sequence may include a probe-hybridizing region contained within the target molecule with which a probe will form a stable hybrid under desired conditions. The "target sequence" may also include the complexing sequences to which the oligonucleotide primers complex and extended using the target sequence as a template. Where the target nucleic acid is originally single-stranded, the term "target sequence" also refers to the sequence complementary to the "target sequence" as present in the target nucleic acid. If the "target nucleic acid" is originally double-stranded, the term "target sequence" refers to both the plus (+) and minus (−) strands.

The term "primer" or "oligonucleotide primer" as used herein, refers to an oligonucleotide which acts to initiate synthesis of a complementary nucleic acid strand when placed under conditions in which synthesis of a primer extension product is induced, i.e., in the presence of nucleotides and a polymerization-inducing agent such as a DNA or RNA polymerase and at suitable temperature, pH, metal concentration, and salt concentration. The primer is preferably single-stranded for maximum efficiency in amplification, but may alternatively be double-stranded. If double-stranded, the primer can first be treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA or RNA synthesis.

As used herein, the term "probe" or "oligonucleotide probe" refers to a structure comprised of a polynucleotide, as defined above, that contains a nucleic acid sequence complementary to a nucleic acid sequence present in the target nucleic acid analyte. The polynucleotide regions of probes may be composed of DNA, and/or RNA, and/or synthetic nucleotide analogs. When an "oligonucleotide probe" is to be used in a 5' nuclease assay, such as the TAQMAN real-time PCR technique, the probe will contain at least one fluorescer and at least one quencher which is digested by the 5' endonuclease activity of a polymerase used in the reaction in order to detect any amplified target oligonucleotide sequences. In this context, the oligonucleotide probe will have a sufficient number of phosphodiester linkages adjacent to its 5' end so that the 5' to 3' nuclease activity employed can efficiently degrade the bound probe to separate the fluorescers and quenchers. When an oligonucleotide probe is used in the TMA technique, it will be suitably labeled, as described below.

It will be appreciated that the hybridizing sequences need not have perfect complementarity to provide stable hybrids. In many situations, stable hybrids will form where fewer than about 10% of the bases are mismatches, ignoring loops of four or more nucleotides. Accordingly, as used herein the term "complementary" refers to an oligonucleotide that forms a stable duplex with its "complement" under assay conditions, generally where there is about 90% or greater homology.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

As used herein, the term "binding pair" refers to first and second molecules that specifically bind to each other, such as complementary polynucleotide pairs capable of forming nucleic acid duplexes. "Specific binding" of the first member of the binding pair to the second member of the binding pair in a sample is evidenced by the binding of the first member to the second member, or vice versa, with greater affinity and specificity than to other components in the sample. The binding between the members of the binding pair is typically noncovalent. Unless the context clearly indicates otherwise, the terms "affinity molecule" and "target analyte" are used herein to refer to first and second members of a binding pair, respectively.

The terms "specific-binding molecule" and "affinity molecule" are used interchangeably herein and refer to a molecule that will selectively bind, through chemical or physical means to a detectable substance present in a sample. By "selectively bind" is meant that the molecule binds preferentially to the target of interest or binds with greater affinity to the target than to other molecules. For example, a DNA molecule will bind to a substantially complementary sequence and not to unrelated sequences.

The "melting temperature" or "Tm" of double-stranded DNA is defined as the temperature at which half of the helical structure of DNA is lost due to heating or other dissociation of the hydrogen bonding between base pairs, for example, by acid or alkali treatment, or the like. The $T_m$ of a DNA molecule depends on its length and on its base composition. DNA molecules rich in GC base pairs have a higher $T_m$ than those having an abundance of AT base pairs. Separated complementary strands of DNA spontaneously reassociate or anneal to form duplex DNA when the temperature is lowered below the $T_m$. The highest rate of nucleic acid hybridization occurs approximately 25° C. below the $T_m$. The $T_m$ may be estimated using the following relationship: $T_m$=69.3+0.41(GC)% (Marmur et al. (1962) *J. Mol. Biol.* 5:109–118).

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, semiconductor nanocrystals, ligands (e.g., biotin, avidin, strepavidin or haptens) and the like. The term "fluorescer" refers to a substance or a portion thereof which is capable of exhibiting fluorescence in the detectable range.

As used herein, a "solid support" refers to a solid surface such as a magnetic bead, latex bead, microtiter plate well, glass plate, nylon, agarose, acrylamide, and the like.

As used herein, a "biological sample" refers to a sample of tissue or fluid isolated from a subject such as, but not limited to, blood, plasma, serum, fecal matter, urine, bone marrow, bile, spinal fluid, lymph fluid, samples of the skin, secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components. The samples detailed above need not necessarily be in the form obtained directly from the source. For example, the sample can be treated prior to use, such as, for example, by heating, centrifuging, etc. prior to analysis.

By "vertebrate subject" is meant any member of the subphylum cordata that is susceptible to WNV infection, including, without limitation, mammals such as horses, and humans, and avian species. The term does not denote a particular age. Thus, adult and newborn animals, as well as fetuses, are intended to be covered.

II. Modes of Carrying out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of compositions and methods similar or equivalent to those described herein can be used in the practice of the present invention, the preferred materials and methods are described herein.

As noted above, the present invention is based on the discovery of novel diagnostic methods for accurately detecting the presence of West Nile virus (WNV) in a biological sample. The methods can be used to detect WNV in a biological sample from any vertebrate species susceptible to the virus. The methods rely on sensitive nucleic acid-based detection techniques that allow identification of WNV target nucleic acid sequences in samples containing small amounts of virus. The methods are particularly useful for detecting WNV in blood samples, including without limitation, in whole blood, serum and plasma. The methods can be used to diagnose WNV infection in a subject, as well as to detect WNV contamination in donated blood samples. Thus, aliquots from individual donated samples or pooled samples can be screened for the presence of WNV and those samples or pooled samples contaminated with WNV can be eliminated before they are combined. In this way, a blood supply substantially free of WNV contamination can be provided. By "substantially free of WNV" is meant that the presence of WNV is not detected using the assays described herein, preferably using the TAQMAN fluorogenic 5' nuclease assays described in the examples. Normally, then, a sample will be considered "substantially free of WNV" when less than 5 copies/ml of WNV target nucleic acid are present, preferably less than 3 copies/ml and even more preferably less than 1 copy/ml.

In the strategy of the present invention, the target nucleic acids are separated from non-homologous nucleic acids using capture oligonucleotides immobilized on a solid support. The capture oligonucleotides are derived from conserved regions of the WNV genome and are specific for WNV. It has been found by the inventors herein that capture oligonucleotides derived from conserved regions of the capsid, prM and 3'UTR regions of the WNV genome are particularly useful in the present diagnostic methods. The sequences for the WNV genome, including these regions, in a number of WNV isolates are known. See, for example, NCBI accession numbers NC001563; AF404757; AF404756; AF404755; AF404754; AF404753; AF481864; M12294; AF196835; AF260969; AF260968; AF260967; AF206518; AF202541; AF196835; Brinton, M. A., *Ann. Rev. Micorbiol.* (2002) 56:371–402; Lanciotti et al., *Science* (1999) 286:2333–2337; and U.S. Patent Publication No. 2002/0164349, all of which are incorporated herein by reference in their entireties. By comparing the sequences from various WNV isolates, these and other conserved regions for use with the present invention can be readily identified.

For convenience, the various nucleotides for use with the present invention have been numbered herein relative to WNV strain WN-NY99 (see, Lanciotti et al., *Science* (1999) 286:2333–2337 and NCBI Accession No. AF196835, for the WN-NY99 genomic sequence).

The separated target nucleic acids can then be detected by the use of oligonucleotide probes, also derived from conserved regions of the WNV genome. The probes can therefore be derived from, for example, conserved regions from the capsid, pr and 3'UTR regions and tagged with reporter groups, or amplified. In order to provide better detection capabilities, more than one probe can be used to account for strain variation. Thus, for example, multiple probes derived from differing major strains of WNV may be used in combination. Following detection, an additional assay can be performed to determine which strain of WNV has caused infection. Additionally, the various probes can be labeled with distinguishable labels to simultaneously detect variants of the virus in a multiplex mode.

Particularly useful capture oligonucleotides comprise the nucleotide sequences of the various oligonucleotides depicted in FIGS. 1A–1R (SEQ ID NOS:1–16, 45, 46 and 50, respectively), or sequences displaying at least about 80–90% or more sequence identity thereto, including any percent identity within these ranges, such as 81, 82, 83, 84, 85, 86, 87, 88, 89, 90, 91, 92, 93, 94, 95, 96, 97, 98, 99% sequence identity thereto. As explained above, the regions from which the capture oligonucleotides are derived are conserved between viral isolates. However, the capture oligonucleotides can be derivatized using methods well known in the art in order to improve the affinity of binding to the target nucleic acid. Particularly useful amplification primers and probes for use on the separated target nucleic acids comprise nucleotide sequences derived from the capsid, E, NS1, NS2 and 3'UTR regions, such as the nucleotide sequences of SEQ ID NOS:34, 35, 37, 38, 42, 43 and 52–55 or sequences displaying at least about 80–90% or more sequence identity thereto, including any percent identity within these ranges.

In one embodiment of the present invention the biological sample potentially carrying target nucleic acid is contacted with a solid support in association with capture oligonucleotides. The capture oligonucleotides, which may be used separately or preferably in combination, may be associated with the solid support, for example, by covalent binding of the capture moiety to the solid support, by affinity association, hydrogen binding, or nonspecific association.

The capture oligonucleotides can include from about 5 to about 500 nucleotides of the particular conserved region, preferably about 10 to about 100 nucleotides, or more preferably about 10 to about 60 nucleotides of the conserved region, or any integer within these ranges, such as a sequence including 18, 19, 20, 21, 22, 23, 24, 25, 26 . . . 35 . . . 40, etc. nucleotides from the conserved region of interest.

The capture oligonucleotide may be attached to the solid support in a variety of manners. For example, the oligonucleotide may be attached to the solid support by attachment of the 3' or 5' terminal nucleotide of the probe to the solid support. More preferably, the capture oligonucleotide is attached to the solid support by a linker which serves to distance the probe from the solid support. The linker is usually at least 10–50 atoms in length, more preferably at least 15–30 atoms in length. The required length of the linker will depend on the particular solid support used. For example, a six atom linker is generally sufficient when high cross-linked polystyrene is used as the solid support.

A wide variety of linkers are known in the art which may be used to attach the oligonucleotide probe to the solid support. The linker may be formed of any compound which does not significantly interfere with the hybridization of the target sequence to the probe attached to the solid support. The linker may be formed of a homopolymeric oligonucleotide which can be readily added on to the linker by automated synthesis. The homopolymeric sequence can be either 5' or 3' to the virus-specific sequence. In one aspect of the invention, the capture oligonucleotides include a homopolymer chain, such as, for example poly A, poly T, poly G, poly C, poly U, poly dA, poly dT, poly dG, poly dC, or poly dU in order to facilitate attachment to a solid support. The homopolymer chain can be from about 10 to about 40 nucleotides in length, or preferably about 12 to about 25 nucleotides in length, or any integer within these ranges, such as for example, 10 . . . 12 . . . 16, 17, 18, 19, 20, 21, 22, 23, or 24 nucleotides. The homopolymer, if present, can be added to the 3' or 5' terminus of the capture oligonucleotides by enzymatic or chemical methods. This addition can be made by stepwise addition of nucleotides or by ligation of a preformed homopolymer.

Particular capture oligonucleotides including poly A chains are shown in the examples and are represented by SEQ ID NOS:18–33, 47, 48 and 51. Preferred capture oligonucleotides are represented by SEQ ID NOS: 8, 12, 45, 46 and 50 (SEQ ID NOS:25, 29, 47, 48 and 51, respectively, with the poly A tail).

Alternatively, polymers such as functionalized polyethylene glycol can be used as the linker. Such polymers do not significantly interfere with the hybridization of probe to the target oligonucleotide. Examples of linkages include polyethylene glycol, carbamate and amide linkages. The linkages between the solid support, the linker and the probe are preferably not cleaved during removal of base protecting groups under basic conditions at high temperature.

The capture oligonucleotide may also be phosphorylated at the 3' end in order to prevent extension of the capture oligonucleotide.

The solid support may take many forms including, for example, nitrocellulose reduced to particulate form and retrievable upon passing the sample medium containing the support through a sieve; nitrocellulose or the materials impregnated with magnetic particles or the like, allowing the nitrocellulose to migrate within the sample medium upon the application of a magnetic field; beads or particles which may be filtered or exhibit electromagnetic properties; and polystyrene beads which partition to the surface of an aqueous medium. Examples of preferred types of solid supports for immobilization of the oligonucleotide probe include controlled pore glass, glass plates, polystyrene, avidin-coated polystyrene beads, cellulose, nylon, acrylamide gel and activated dextran.

A preferred embodiment of the present invention includes a solid support comprising magnetic beads. Preferably, the magnetic beads contain primary amine functional groups which facilitate covalent binding or association of the capture oligonucleotides to the magnetic support particles. Alternatively, the magnetic beads have immobilized thereon homopolymers, such as poly T or poly A sequences. The homopolymers on the solid support will generally be complementary to any homopolymer on the capture oligonucleotide to allow attachment of the capture oligonucleotide to the solid support by hybridization. The use of a solid support with magnetic beads allows for a one-pot method of isolation, amplification and detection as the solid support can be separated from the biological sample by magnetic means.

The magnetic beads or particles can be produced using standard techniques or obtained from commercial sources. In general, the particles or beads may be comprised of magnetic particles, although they can also include other magnetic metal or metal oxides, whether in impure, alloy, or composite form, as long as they have a reactive surface and exhibit an ability to react to a magnetic field. Other materials that may be used individually or in combination with iron include, but are not limited to, cobalt, nickel, and silicon. A magnetic bead suitable for use with the present invention includes magnetic beads containing poly dT groups marketed under the trade name SERA-MAG magnetic oligonucleotide beads by Seradyn, Indianapolis, Ind.

Next, the association of the capture oligonucleotides with the solid support is initiated by contacting the solid support with the medium containing the capture oligonucleotides. In the preferred embodiment, the magnetic beads containing poly dT groups are hybridized with the capture oligonucleotides that comprise poly dA contiguous with the capture sequence (i.e., the sequence substantially complementary to a WNV nucleic acid sequence) selected from the conserved single stranded region of the WNV genome. The poly dA on the capture oligonucleotide and the poly dT on the solid support hybridize thereby immobilizing or associating the capture oligonucleotides with the solid support.

The solid support with associated capture oligonucleotides is brought into contact with the biological sample under hybridizing conditions. The capture oligonucleotides hybridize to the target strands present in the biological sample. Typically, hybridization of capture oligonucleotides to the targets can be accomplished in approximately 15 minutes, but may take as long as 3 to 48 hours.

The solid support is then separated from the biological sample, for example, by filtering, passing through a column, or by magnetic means. As will be appreciated by one of skill in the art, the method of separation will depend on the type of solid support selected. Since the targets are hybridized to the capture oligonucleotides immobilized on the solid support, the target strands are thereby separated from the impurities in the sample. In some cases, extraneous nucleic acids, proteins, carbohydrates, lipids, cellular debris, and other impurities may still be bound to the support, although at much lower concentrations than initially found in the biological sample. Those skilled in the art will recognize that some undesirable materials can be removed by washing the support with a washing medium. The separation of the solid support from the biological sample preferably removes at least about 70%, more preferably about 90% and, most preferably, at least about 95% or more of the non-target nucleic acids present in the sample.

The methods of the present invention may also include amplifying the captured target WNV nucleic acid to produce amplified nucleic acids. Amplifying a target nucleic acid typically uses a nucleic acid polymerase to produce multiple copies of the target nucleic acid or fragments thereof. Suitable amplification techniques are well known in the art, such as, for example transcription mediated amplification, polymerase chain reaction (PCR), replicase mediated amplification, and ligase chain reaction (LCR).

Capture oligonucleotides, primers and probes for use in the assays are readily synthesized by standard techniques, e.g., solid phase synthesis via phosphoramidite chemistry, as disclosed in U.S. Pat. Nos. 4,458,066 and 4,415,732, incorporated herein by reference in their entireties; Beaucage et al. (1992) *Tetrahedron* 48:2223–2311; and Applied Biosystems User Bulletin No. 13 (1 Apr. 1987). Other chemical synthesis methods include, for example, the phosphotriester method described by Narang et al., *Meth. Enzymol.* (1979) 68:90 and the phosphodiester method disclosed by Brown et al., *Meth. Enzymol.* (1979) 68:109. Poly A or poly C, or other non-complementary nucleotide extensions may be incorporated into probes using these same methods. Hexaethylene oxide extensions may be coupled to probes by methods known in the art. Cload et al. (1991) *J. Am. Chem. Soc.* 113:6324–6326; U.S. Pat. No. 4,914,210 to Levenson et al.; Durand et al. (1990) *Nucleic Acids Res.* 18:6353–6359; and Horn et al. (1986) *Tet. Lett.* 27:4705–4708.

Moreover, the primers and probes may be coupled to labels for detection. There are several means known for derivatizing oligonucleotides with reactive functionalities which permit the addition of a label. For example, several approaches are available for biotinylating probes so that radioactive, fluorescent, chemiluminescent, enzymatic, or electron dense labels can be attached via avidin. See, e.g., Broken et al., *Nucl. Acids Res.* (1978) 5:363–384 which discloses the use of ferritin-avidin-biotin labels; and Chollet et al. *Nucl. Acids Res.* (1985) 13:1529–1541 which discloses biotinylation of the 5' termini of oligonucleotides via an aminoalkylphosphoramide linker arm. Several methods are also available for synthesizing amino-derivatized oligonucleotides which are readily labeled by fluorescent or other types of compounds derivatized by amino-reactive groups, such as isothiocyanate, N-hydroxysuccinimide, or the like, see, e.g., Connolly (1987) *Nucl. Acids Res.* 15:3131–3139, Gibson et al. (1987) *Nucl. Acids Res.* 15:6455–6467 and U.S. Pat. No. 4,605,735 to Miyoshi et al. Methods are also available for synthesizing sulfhydryl-derivatized oligonucleotides which can be reacted with thiol-specific labels, see, e.g., U.S. Pat. No. 4,757,141 to Fung et al., Connolly et al. (1985) *Nucl. Acids Res.* 13:4485–4502 and Spoat et al. (1987) *Nucl. Acids Res.* 15:4837–4848. A comprehensive review of methodologies for labeling DNA fragments is provided in Matthews et al., *Anal. Biochem.* (1988) 169: 1–25.

For example, primers and probes may be fluorescently labeled by linking a fluorescent molecule to the non-ligating terminus of the probe. Guidance for selecting appropriate fluorescent labels can be found in Smith et al., *Meth. Enzymol.* (1987) 155:260–301; Karger et al., *Nucl. Acids Res.* (1991) 19:4955–4962; Haugland (1989) *Handbook of Fluorescent Probes and Research Chemicals* (Molecular Probes, Inc., Eugene, Oreg.). Preferred fluorescent labels include fluorescein and derivatives thereof, such as disclosed in U.S. Pat. No. 4,318,846 and Lee et al., *Cytometry* (1989) 10:151-164, and 6-FAM, JOE, TAMRA, ROX, HEX-1, HEX-2, ZOE, TET-1 or NAN-2, and the like.

Additionally, primers and probes can be labeled with an acridinium ester (AE) using the techniques described below. Current technologies allow the AE label to be placed at any location within the probe. See, e.g., Nelson et al. (1995) "Detection of Acridinium Esters by Chemiluminescence" in *Nonisotopic Probing, Blotting and Sequencing*, Kricka L. J. (ed) Academic Press, San Diego, Calif.; Nelson et al. (1994) "Application of the Hybridization Protection Assay (HPA) to PCR" in *The Polymerase Chain Reaction*, Mullis et al. (eds.) Birkhauser, Boston, Mass.; Weeks et al., *Clin. Chem.* (1983) 29:1474–1479; Berry et al., *Clin. Chem.* (1988) 34:2087–2090. An AE molecule can be directly attached to the probe using non-nucleotide-based linker arm chemistry that allows placement of the label at any location within the probe. See, e.g., U.S. Pat. Nos. 5,585,481 and 5,185,439.

In certain embodiments, an internal control (IC) or an internal standard is added to serve as a control for target capture and amplification. Preferably, the IC includes a sequence that differs from the target sequences, is capable of hybridizing with the capture oligonucleotides used for separating the nucleic acids specific for the organism from the sample, and is capable of amplification by the primers used to amplify the target WNV nucleic acids. The use of the internal control permits the control of the separation process, the amplification process, and the detection system, and permits the monitoring of the assay performance and quantization for the sample(s). The amplification control can be distinguished from the amplified target (here WNV) in the detection step. Different probes can be used for the detection of the control and the target. The IC can be included at any suitable point, for example, in the lysis buffer. In one embodiment, the IC comprises RNA containing a part of the WNV nucleotide sequence and a unique sequence that hybridizes with the probe. Thus, in certain embodiments, the IC includes a portion of the WNV genome with a modified sequence with 5–30, such as 6 . . . 9 . . . 12 . . . 15 . . . 20 and so on or more bases substituted with other bases. The substitute bases can be located over the entire length of the target sequence such that only 2 or 3 consecutive sequences are replaced. A representative IC for WNV is shown in FIG. 2 (SEQ ID NO:17) and comprises 967 bps derived from the 5' UTR and 5' coding region of the WNV genome. The bolded, upper case bases in FIG. 2 represent substituted bases that have been substituted for the bases occurring in the WNV wild-type sequence in question. The assay may additionally include probes specific to the internal standard (IC probe).

Representative probes for the IC sequence are detailed in the examples as SEQ ID NO:40 and SEQ ID NO:41. The IC probe can optionally be coupled with a detectable label that is different from the detectable label for the target sequence. In embodiments where the detectable label is a fluorophore, the IC can be quantified spectrophorometrically and by limit of detection studies. One exemplary IC probe for attachment to the solid support is represented by the sequence xCAGT-GACATGCAGGTCTAGCTz (SEQ ID NO:40), where x=TET and z=linker+TAMRA. Another exemplary IC probe for attachment to the solid support is represented by the sequence xCCCAGTGACATGCAGGTCTAGCTz (SEQ ID NO:41), where x=TET and z=linker+TAMRA.

Typically, the copy number of IC which does not interfere with the target detection is determined by titrating the IC with a fixed IU/copies/PFU of target, preferably at the lower end, and a standard curve is generated by diluting a sample of internationally accepted standard.

In another embodiment, an IC comprising RNA, as described herein, is combined with nucleic acid isolated from the sample according to standard techniques known to those of skill in the art. The RNA is then reverse transcribed using a reverse transcriptase to provide cDNA. The cDNA sequences can be optionally amplified (e.g., by PCR) using labeled primers. The amplification products are separated, typically by electrophoresis, and the amount of incorporated label (proportional to the amount of amplified product) is determined. The amount of RNA in the sample is then calculated by comparison with the signal produced by the known standards.

The primers and probes described above may be used in polymerase chain reaction (PCR)-based techniques, such as RT-PCR, to detect the presence of WNV in biological samples. PCR is a technique for amplifying a desired target nucleic acid sequence contained in a nucleic acid molecule or mixture of molecules. In PCR, a pair of primers is employed in excess to hybridize to the complementary strands of the target nucleic acid. The primers are each extended by a polymerase using the target nucleic acid as a template. The extension products become target sequences themselves after dissociation from the original target strand. New primers are then hybridized and extended by a polymerase, and the cycle is repeated to geometrically increase the number of target sequence molecules. The PCR method for amplifying target nucleic acid sequences in a sample is well known in the art and has been described in, e.g., Innis et al. (eds.) *PCR Protocols* (Academic Press, NY 1990); Taylor (1991) *Polymerase chain reaction: basic principles and automation*, in *PCR: A Practical Approach*, McPherson et al. (eds.) IRL Press, Oxford; Saiki et al. (1986) Nature 324:163; as well as in U.S. Pat. Nos. 4,683,195, 4,683,202 and 4,889,818, all incorporated herein by reference in their entireties.

In particular, PCR uses relatively short oligonucleotide primers which flank the target nucleotide sequence to be amplified, oriented such that their 3' ends face each other, each primer extending toward the other. The polynucleotide sample is extracted and denatured, preferably by heat, and hybridized with first and second primers which are present in molar excess. Polymerization is catalyzed in the presence of the four deoxyribonucleotide triphosphates (dNTPs—dATP, dGTP, dCTP and dTTP) using a primer- and template-dependent polynucleotide polymerizing agent, such as any enzyme capable of producing primer extension products, for example, *E. coli* DNA polymerase I, Klenow fragment of DNA polymerase I, T4 DNA polymerase, thermostable DNA polymerases isolated from *Thermus aquaticus* (Taq), available from a variety of sources (for example, Perkin Elmer), *Thermus thermophilus* (United States Biochemicals), *Bacillus stereothermophilus* (Bio-Rad), or *Thermococcus litoralis* ("Vent" polymerase, New England Biolabs). This results in two "long products" which contain the respective primers at their 5' ends covalently linked to the newly synthesized complements of the original strands. The reaction mixture is then returned to polymerizing conditions, e.g., by lowering the temperature, inactivating a denaturing agent, or adding more polymerase, and a second cycle is initiated. The second cycle provides the two original strands, the two long products from the first cycle, two new long products replicated from the original strands, and two "short products" replicated from the long products. The short products have the sequence of the target sequence with a primer at each end. On each additional cycle, an additional two long products are produced, and a number of short products equal to the number of long and short products remaining at the end of the previous cycle. Thus, the number of short products containing the target sequence grow exponentially with each cycle. Preferably, PCR is carried out with a commercially available thermal cycler, e.g., Perkin Elmer.

RNAs may be amplified by reverse transcribing the mRNA into cDNA, and then performing PCR (RT-PCR), as described above. Alternatively, a single enzyme may be used for both steps as described in U.S. Pat. No. 5,322,770. mRNA may also be reverse transcribed into cDNA, followed by asymmetric gap ligase chain reaction (RT-AGLCR) as described by Marshall et al. (1994) *PCR Meth. App.* 4:80–84.

The fluorogenic 5' nuclease assay, known as the TAQ-MAN real-time PCR assay (see, e.g., Holland et al., *Proc. Natl. Acad. Sci. USA* (1991) 88:7276–7280), is a powerful and versatile PCR-based detection system for nucleic acid targets. Hence, primers and probes derived from conserved regions of the WNV genome described herein can be used in TAQMAN real-time PCR analyses to detect the presence of WNV in a biological sample. Analysis is performed in conjunction with thermal cycling by monitoring the generation of fluorescence signals. The assay system dispenses with the need for gel electrophoretic analysis, and has the capability to generate quantitative data allowing the determination of target copy numbers. For example, standard curves can be produced using serial dilutions of previously quantified viral suspensions of WNV. A standard graph can be produced with copy numbers of each of the panel members against which sample unknowns can be compared.

The fluorogenic 5' nuclease assay is conveniently performed using, for example, AmpliTaq Gold™ DNA polymerase, which has endogenous 5' nuclease activity, to digest an internal oligonucleotide probe labeled with both a fluorescent reporter dye and a quencher (see, Holland et al., *Proc. Natl. Acad. Sci. USA* (1991) 88:7276–7280; and Lee et al., *Nucl. Acids Res.* (1993) 21:3761–3766). Assay results are detected by measuring changes in fluorescence that occur during the amplification cycle as the fluorescent probe is digested, uncoupling the dye and quencher labels and causing an increase in the fluorescent signal that is proportional to the amplification of target nucleic acid.

The amplification products can be detected in solution or using solid supports. In this method, the TAQMAN probe is designed to hybridize to a target sequence within the desired PCR product. The 5' end of the TAQMAN probe contains a fluorescent reporter dye. The 3' end of the probe is blocked to prevent probe extension and contains a dye that will quench the fluorescence of the 5' fluorophore. During subsequent amplification, the 5' fluorescent label is cleaved off if a polymerase with 5' exonuclease activity is present in the reaction. Excision of the 5' fluorophore results in an increase in fluorescence which can be detected. Representative labeled probes include the probes of SEQ ID NOS:36, 39, 44 and 49.

For a detailed description of the TAQMAN fluorogenic 5' nuclease assay, reagents and conditions for use therein, see, e.g., Holland et al., *Proc. Natl. Acad. Sci, U.S.A.* (1991) 88:7276–7280; U.S. Pat. Nos. 5,538,848, 5,723,591, and 5,876,930, all incorporated herein by reference in their entireties.

Accordingly, the present invention relates to methods for amplifying a target WNV nucleotide sequence using a nucleic acid polymerase having 5' to 3' nuclease activity, one or more primers capable of hybridizing to the WNV target sequence, and an oligonucleotide probe capable of hybridizing to the WNV target sequence 3' relative to the primer. During amplification, the polymerase digests the oligonucleotide probe when it is hybridized to the target sequence, thereby separating the reporter molecule from the quencher molecule. As the amplification is conducted, the fluorescence of the reporter molecule is monitored, with fluorescence corresponding to the occurrence of nucleic acid amplification. The reporter molecule is preferably a fluorescein dye and the quencher molecule is preferably a rhodamine dye.

While the length of the primers and probes can vary, the probe sequences are selected such that they have a higher melt temperature than the primer sequences. Preferably, the probe sequences have an estimated melt temperature that is about 10° C. higher than the melt temperature for the amplification primer sequences. Hence, the primer sequences are generally shorter than the probe sequences. Typically, the primer sequences are in the range of between 10–75 nucleotides long, more typically in the range of 20–45. The typical probe is in the range of between 10–50 nucleotides long, more typically 15–40 nucleotides in length.

The WNV sequences described herein may also be used as a basis for transcription-mediated amplification (TMA) assays. TMA provides a method of identifying target nucleic acid sequences present in very small amounts in a biological sample. Such sequences may be difficult or impossible to detect using direct assay methods. In particular, TMA is an isothermal, autocatalytic nucleic acid target amplification system that can provide more than a billion RNA copies of a target sequence. The assay can be done qualitatively, to accurately detect the presence or absence of the target sequence in a biological sample. The assay can also provide a quantitative measure of the amount of target sequence over a concentration range of several orders of magnitude. TMA provides a method for autocatalytically synthesizing multiple copies of a target nucleic acid sequence without repetitive manipulation of reaction conditions such as temperature, ionic strength and pH.

Generally, TMA includes the following steps: (a) isolating nucleic acid, including RNA, from the biological sample of interest suspected of being infected with WNV; and (b) combining into a reaction mixture (i) the isolated nucleic acid, (ii) first and second oligonucleotide primers, the first primer having a complexing sequence sufficiently complementary to the 3' terminal portion of an RNA target sequence, if present (for example the (+) strand), to complex therewith, and the second primer having a complexing sequence sufficiently complementary to the 3' terminal portion of the target sequence of its complement (for example, the (−) strand) to complex therewith, wherein the first oligonucleotide further comprises a sequence 5' to the complexing sequence which includes a promoter, (iii) a reverse transcriptase or RNA and DNA dependent DNA polymerases, (iv) an enzyme activity which selectively degrades the RNA strand of an RNA-DNA complex (such as an RNAse H) and (v) an RNA polymerase which recognizes the promoter.

The components of the reaction mixture may be combined stepwise or at once. The reaction mixture is incubated under conditions whereby an oligonucleotide/target sequence is formed, including DNA priming and nucleic acid synthesizing conditions (including ribonucleotide triphosphates and deoxyribonucleotide triphosphates) for a period of time sufficient to provide multiple copies of the target sequence. The reaction advantageously takes place under conditions suitable for maintaining the stability of reaction components such as the component enzymes and without requiring modification or manipulation of reaction conditions during the course of the amplification reaction. Accordingly, the reaction may take place under conditions that are substantially isothermal and include substantially constant ionic strength and pH. The reaction conveniently does not require a denaturation step to separate the RNA-DNA complex produced by the first DNA extension reaction.

Suitable DNA polymerases include reverse transcriptases, such as avian myeloblastosis virus (AMV) reverse transcriptase (available from, e.g., Seikagaku America, Inc.) and Moloney murine leukemia virus (MMLV) reverse transcriptase (available from, e.g., Bethesda Research Laboratories).

Promoters or promoter sequences suitable for incorporation in the primers are nucleic acid sequences (either naturally occurring, produced synthetically or a product of a restriction digest) that are specifically recognized by an RNA polymerase that recognizes and binds to that sequence and initiates the process of transcription whereby RNA transcripts are produced. The sequence may optionally include nucleotide bases extending beyond the actual recognition site for the RNA polymerase which may impart added stability or susceptibility to degradation processes or increased transcription efficiency. Examples of useful promoters include those which are recognized by certain bacteriophage polymerases such as those from bacteriophage T3, T7 or SP6, or a promoter from *E. coli*. These RNA polymerases are readily available from commercial sources, such as New England Biolabs and Epicentre.

Some of the reverse transcriptases suitable for use in the methods herein have an RNAse H activity, such as AMV reverse transcriptase. It may, however, be preferable to add exogenous RNAse H, such as *E. coli* RNAse H, even when AMV reverse transcriptase is used. RNAse H is readily available from, e.g., Bethesda Research Laboratories.

The RNA transcripts produced by these methods may serve as templates to produce additional copies of the target sequence through the above-described mechanisms. The system is autocatalytic and amplification occurs autocatalytically without the need for repeatedly modifying or changing reaction conditions such as temperature, pH, ionic strength or the like.

Detection may be done using a wide variety of methods, including direct sequencing, hybridization with sequence-specific oligomers, gel electrophoresis and mass spectrometry. these methods can use heterogeneous or homogeneous formats, isotopic or nonisotopic labels, as well as no labels at all.

One preferable method of detection is the use of target sequence-specific oligonucleotide probes described above. The probes may be used in hybridization protection assays (HPA). In this embodiment, the probes are conveniently labeled with acridinium ester (AE), a highly chemiluminescent molecule. See, e.g., Nelson et al. (1995) "Detection of Acridinium Esters by Chemiluminescence" in *Nonisotopic Probing, Blotting and Sequencing*, Kricka L. J. (ed) Academic Press, San Diego, Calif.; Nelson et al. (1994) "Application of the Hybridization Protection Assay (HPA) to PCR" in *The Polymerase Chain Reaction*, Mullis et al. (eds.) Birkhauser, Boston, Mass.; Weeks et al., *Clin. Chem.* (1983) 29:1474–1479; Berry et al., *Clin. Chem.* (1988) 34:2087–2090. One AE molecule is directly attached to the probe using a non-nucleotide-based linker arm chemistry that allows placement of the label at any location within the probe. See, e.g., U.S. Pat. Nos. 5,585,481 and 5,185,439. Chemiluminescence is triggered by reaction with alkaline hydrogen peroxide which yields an excited N-methyl acridone that subsequently collapses to ground state with the emission of a photon.

When the AE molecule is covalently attached to a nucleic acid probe, hydrolysis is rapid under mildly alkaline conditions. When the AE-labeled probe is exactly complementary to the target nucleic acid, the rate of AE hydrolysis is greatly reduced. Thus, hybridized and unhybridized AE-labeled probe can be detected directly in solution, without the need for physical separation.

HPA generally consists of the following steps: (a) the AE-labeled probe is hybridized with the target nucleic acid in solution for about 15 to about 30 minutes. A mild alkaline solution is then added and AE coupled to the unhybridized probe is hydrolyzed. This reaction takes approximately 5 to 10 minutes. The remaining hybrid-associated AE is detected as a measure of the amount of target present. This step takes approximately 2 to 5 seconds. Preferably, the differential hydrolysis step is conducted at the same temperature as the hybridization step, typically at 50 to 70° C. Alternatively, a second differential hydrolysis step may be conducted at room temperature. This allows elevated pHs to be used, for example in the range of 10–11, which yields larger differences in the rate of hydrolysis between hybridized and unhybridized AE-labeled probe. HPA is described in detail in, e.g., U.S. Pat. Nos. 6,004,745; 5,948,899; and 5,283,174, the disclosures of which are incorporated by reference herein in their entireties.

TMA is described in detail in, e.g., U.S. Pat. No. 5,399,491, the disclosure of which is incorporated herein by reference in its entirety. In one example of a typical assay, an isolated nucleic acid sample, suspected of containing a WNV target sequence, is mixed with a buffer concentrate containing the buffer, salts, magnesium, nucleotide triphosphates, primers, dithiothreitol, and spermidine. The reaction is optionally incubated at about 100° C. for approximately two minutes to denature any secondary structure. After cooling to room temperature, reverse transcriptase, RNA polymerase, and RNAse H are added and the mixture is incubated for two to four hours at 37° C. The reaction can then be assayed by denaturing the product, adding a probe solution, incubating 20 minutes at 60° C., adding a solution to selectively hydrolyze the unhybridized probe, incubating the reaction six minutes at 60° C., and measuring the remaining chemiluminescence in a luminometer.

In another aspect of the invention, two or more of the tests described above are performed to confirm the presence of the organism. For example, if the first test used the transcription mediated amplification (TMA) to amplify the nucleic acids for detection, then an alternative nucleic acid testing (NAT) assay is performed, for example, by using PCR amplification, RT PCR, and the like, as described herein. Thus, WNV can be specifically and selectively detected even when the sample contains other organisms, such as HIV, and parvovirus B19, for example.

As is readily apparent, design of the assays described herein are subject to a great deal of variation, and many formats are known in the art. The above descriptions are merely provided as guidance and one of skill in the art can readily modify the described protocols, using techniques well known in the art.

The above-described assay reagents, including the primers, probes, solid support with bound probes, as well as other detection reagents, can be provided in kits, with suitable instructions and other necessary reagents, in order to conduct the assays as described above. The kit will normally contain in separate containers the combination of primers and probes (either already bound to a solid matrix or separate with reagents for binding them to the matrix), control formulations (positive and/or negative), labeled reagents when the assay format requires same and signal generating reagents (e.g., enzyme substrate) if the label does not generate a signal directly. Instructions (e.g., written, tape, VCR, CD-ROM, etc.) for carrying out the assay usually will be included in the kit. The kit can also contain, depending on the particular assay used, other packaged reagents and materials (i.e. wash buffers and the like). Standard assays, such as those described above, can be conducted using these kits.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

In the following examples, enzymes were purchased from commercial sources, and used according to the manufacturers' directions. Nitrocellulose filters and the like were also purchased from commercial sources.

In the isolation of DNA fragments, except where noted, all DNA manipulations were done according to standard procedures. See, Sambrook et al., supra. Restriction enzymes, $T_4$ DNA ligase, *E. coli*, DNA polymerase I, Klenow fragment, and other biological reagents can be purchased from commercial suppliers and used according to the manufacturers' directions. Double stranded DNA fragments were separated on agarose gels.

EXAMPLE 1

Extraction of WNV RNA from the Biological Sample

WNV nucleic acid-positive tissue culture was purchased from Boston Biomedica, Inc. Two approaches were used to isolate nucleic acid from 0.5 ml of sample. In particular, RNA was extracted by (a) binding to silica; and (b) annealing to target-specific oligonucleotides.

(a) Isolation of Nucleic Acid by Binding to Silica.

The method described by Boom et al. (1990) *J. Clin. Microbiol.* 28:495–503 was generally followed. In the presence of high concentrations of chaotropic salt such as guanidinium isothiocyanate, nucleic acids bind to silica. Small sized nucleic acids bind more efficiently to silica under conditions of acidic pH. The bound nucleic acids are efficiently eluted in low salt, alkaline pH buffer at high temperatures. The substitution of magnetized silica for regular silica greatly facilitates the washing and elution steps of nucleic acid isolation. Thus, a magnetic base was used to capture the nucleic acid-bound silica particles, thus eliminating centrifugations required to sediment regular silica particles.

The lysis buffer used was from Organon-Teknika (Durham, N.C.). This lysis buffer contained guanidinium isothiocyanate to solubilize proteins and inactivate RNases and DNases, and Triton X-100. The detergent Triton X-100 further facilitated the process of solubilization and disintegration of cell structure and nuclear proteins, thus releasing nucleic acid. In particular, the cultured WNV was serially diluted using serum from Seracure (Ocean Side, Calif.). Pre-aliquoted 9.0 ml of the lysis reagent was used to extract RNA from 0.5 ml of the WNV-positive serum ($10^5$/ml). Magnetized silica MAGPREP particles, Novagen, Wis.) was substituted for regular silica and magnetic base was used to capture the nucleic acid-bound silica particles, thus eliminating centrifugations required to sediment regular silica particles. The bound nucleic acids were eluted in 50 µl of 10 mM Tris pH 8.0 containing 1 mM EDTA. Following nucleic acid isolation, the presence of WNV was determined by performing TAQMAN RT-PCR, as described below.

(b) Isolation of Nucleic Acid by Annealing to Target-Specific Oligonucleotides.

Although use of magnetized silica greatly facilitates rapid and easy handling during the washing and elution steps, isolation of nucleic acid is still laborious and time consuming. Therefore one-step capture of specific nucleic acid target from plasma or serum using magnetic beads was used. In order to make this applicable for a wide variety of viral nucleic acid capture tests, generic magnetic beads coupled with oligo dT were used. SERA-MAG magnetic oligo (dT) beads (Seradyn, Indianapolis, Ind.) with an oligo dT length of about 14 bps, were used in combination with Capture oligonucleotides containing from 21–24 poly A's at the 3' end contiguous with the WNV-specific sequence used (designated at the end of the sequence specified below).

The magnetic beads were suspended in 0.4 ml of lysis buffer which contained 200 µl of Organon-Teknika (Durham, N.C.) lysis buffer (see, Example 1 (a)) and 200 µl of 2× lysis buffer containing 10 mM EDTA, 2% Triton X-102, 100 mM Hepes pH 7.5, 2.0 M $LiCl_2$. An alternative lysis buffer included a lysis buffer which contained 200 µl of Promega (Madison, Wisc.) lysis buffer and 200 µl of 2× lysis buffer containing 10 mM EDTA, 2% Triton X-102, 100 mM Hepes pH 7.5, 2.0 M $LiCl_2$. Another lysis buffer included 400 µl of 5 mM EDTA, 1% Triton X-102, 50 mM Hepes pH 7.5, 2.0 M $LiCl_2$, and 5.0 M guanidinium thiocyanate.

The capture primers were tested individually or in combination, to capture 100 copies/ml of WNV RNA. Following capture, the beads were washed three times with a wash buffer of 10 mM Hepes (pH 7.5), 0.5% NP-40 containing 0.3 M NaCl. The beads with the captured nucleic acid were suspended in 100 µl of TAQMAN one-step RT-PCR reagent and transferred to a TAQMAN RT-PCR microtiter plate for detection by TAQMAN PCR as described below. Several oligonucleotide combinations were efficient at capturing WNV as detected by the TAQMAN PCR assay.

The capture oligonucleotides used were as follows (the numbering indicated at the end of the sequence corresponds to the position within the WNV genome, relative to NCBI accession number AF196835):

```
VWNVC1-aaaaaaaaaaaaaaaaaaaaaagcacatgtatcccacatccattg (nt 578-600)    (SEQ ID NO:18)

VWNVC2-aaaaaaaaaaaaaaaaaaaaaactctgacaatgcataggttctttt (nt 555-577)   (SEQ ID NO:19)

VWNVC3-aaaaaaaaaaaaaaaaaaaaaaccagcagctgttggaatcgtg (nt 534-554)      (SEQ ID NO:20)

VWNVC4-aaaaaaaaaaaaaaaaaaaaaatgacatctgtgacgtcagtagc (nt 511-532)     (SEQ ID NO:21)

VWNVC5-aaaaaaaaaaaaaaaaaaaaaatttaccgtcatcatcaccttccc (nt 487-509)    (SEQ ID NO:22)

VWNVC6-aaaaaaaaaaaaaaaaaaaaaattggaagttagagagggtaactg (nt 464-486)    (SEQ ID NO:23)

VWNVC7-aaaaaaaaaaaaaaaaaaaaaactcctacgctggcgatcaggcc (nt 442-463)     (SEQ ID NO:24)

VWNVC8-aaaaaaaaaaaaaaaaaaaaaaatcatgactgcaattccggtcttt (nt 421-441)   (SEQ ID NO:25)

VWNVC9-aaaaaaaaaaaaaaaaaaaaaagagctccgccgattgatagca (nt 375-395)      (SEQ ID NO:26)

VWNVC10-aaaaaaaaaaaaaaaaaaaaaactggtcaaggtccctagttcc (nt 354-374)     (SEQ ID NO:27)

VWNVC11-aaaaaaaaaaaaaaaaaaaaaattcttaaaactcagaaggtgtttca (nt 329-353) (SEQ ID NO:28)

VWNVC12-aaaaaaaaaaaaaaaaaaaaaatcgctgtttgtttgttcacacctc (nt 305-328)  (SEQ ID NO:29)

VWNVC13-aaaaaaaaaaaaaaaaaaaaaatccatcgatccagcactgctcgggtc (nt 279-304) (SEQ ID NO:30)
```

```
VWNVC14-aaaaaaaaaaaaaaaaaaaaaggagcaattgctgtgaacctgaa (nt 256-278)      (SEQ ID NO:31)

VWNVC15-aaaaaaaaaaaaaaaaaaaaagaacgccaagagagccaacac (nt 235-255)        (SEQ ID NO:32)

VWNVC16-aaaaaaaaaaaaaaaaaaaaaaatcgtattggccccttgccgtcg (nt 210-234)     (SEQ ID NO:33)

VWNVC45-gtccacctcttgcgaaggacaaaaaaaaaaaa (nt 3592-3612)                (SEQ ID NO:47)

VWNVC46-ctgtgccgtgtggctggttgtaaaaaaaaaaa (nt 10,967-10,988)            (SEQ ID NO:48)

VWNVC18-cctagtctatcccaggtgtcaaaaaaaaaaaaaaaaaaaaa (nt 10,931-10,950)   (SEQ ID NO:51)
```

EXAMPLE 2

Detection and Quantitation of WNV Nucleic Acid by TAQMAN PCR

TAQMAN real-time PCR technology was used for amplifying the captured target as DNA. For this amplification, three sets of oligonucleotides were derived from conserved regions within the capsid (VWNVA1–VWNVA3), 3'UTR (VWNVA4–VWNVA6), and NS1/NS2 region (VWNVA7–VWNVA9) of the WNV genome. The primer and probe sets were as follows (the numbering indicated at the end of the sequence corresponds to the position within the WNV genome, relative to NCBI accession number AF196835):

```
VWNVA1-CCGGGCTGTCAATATGCTAAA      (SEQ ID NO:34)
(Sense Primer-nt129-149)

VWNVA2-AGCCCTCTTCAGTCCAATCAAG     (SEQ ID NO:35)
(Antisense Primer-nt174-195)

VWNVA3-xCGGAATGCCCCGCGTGTTGz      (SEQ ID NO:36)
(Probe-nt153-171)
```

A second probe may also be used in combination with the first probe in order compensate for strain variation and provide greater detection capabilities. A representative second probe has the following sequence:

```
x-CGGTATGCCCCGCGGATTG-z           (SEQ ID NO:49)
(Probe- nt 153-171)

VWNVA4-CAGACCACGCTACGGCG          (SEQ ID NO:37)
(Sense Primer-nt10668-10684)

VWNVA5-CTAGGGCCGCGTGGG            (SEQ ID NO:38)
(Antisense Primer-nt10756-10770)

VWNVA6-xTCTGCGGAGAGTGCAGTCTGCGATz (SEQ ID NO:39)
(Probe-nt10691-10714)

VWNVA7-TCTGCTCTTCCTCTCCGTGAA      (SEQ ID NO:42)
(Sense Primer-nt2439-2460)

VWNVA8-CTCTTGCCGGCTGATGTCTAT      (SEQ ID NO:43)
(antisense primer-nt2485-2506)

VWNVA9-xTGCACGCTGACACTGGGTGTGCz   (SEQ ID NO:44)
(Probe-nt2462-2484)
```

In the sequences above, x=6-FAM and z=linker plus TAMRA.

Reagents for the TAQMAN real-time PCR analysis were obtained from Applied Biosystems, Foster City, Calif. The nucleic acid from Example 1 (a) in a 47 μl volume was used in the TAQMAN real-time PCR assay in a total volume of 100 μl by adding 2× one-step RT-PCR master mix reagent containing 0.4 pmol of the probe. Alternatively, 100 μl of the 1× one-step RT-PCR master mix reagent containing 1 pmol of each of the amplification primers, and 0.4 pmol of the probe, was added to target captured on the magnetic beads and the suspension transferred to a TAQMAN microtiter plate. The reaction conditions were 48° C. for 30 min for the RT reaction, 10 min at 95° C. to activate the enzyme followed by 50 cycles of 30 seconds at 95° C., alternating with 1 min at 60° C. in an ABI 7900 Sequence Detector. The two sets of oligonucleotides described above were used.

Using the protocol of target with capture primers and TAQMAN RT-PCR technology, as few as 10 copies of the target could be detected.

An internal control transcript of 967 bps, FIG. 2 (SEQ ID NO:17), which can be captured by the capture oligonucleotides and amplifiable by VWNAV1 and VWNAV2 but with an altered probe-binding sequence was prepared. The internal control is useful for determining false negatives. The bolded letters in the sequence depicted in FIG. 2 represent the sequence in the IC that replaces the sequence in the target. The probe sequence for the IC is xCAGTGACATG-CAGGTCTAGCTz (SEQ ID NO:40) or xCCCAGTGA-CATGCAGGTCTAGCTz (SEQ ID NO:41) where x=TET and z=linker+TAMRA.

EXAMPLE 3

Testing Amplification Efficiency

The WNV RNA isolated by binding to silica was amplified in the TAQMAN real-time PCR assay and detected using the methods, primers and probes described above. Typically, signals from samples realized <45 cycles at a threshold of >0.2 were considered positive. Table 1 details the results.

TABLE 1

| Region | Ct | Ct |
|---|---|---|
| Capsid | 32.43 | Average = 32.56 |
|  | 32.63 | Std Dev = 0.11 |
|  | 32.61 | % CV = 0.34 |
| NS1/NS2 | 33.90 | Average = 33.31 |
|  | 32.93 | Std Dev = 0.52 |
|  | 33.10 | % CV = 1.56 |
| 3'UTR | 32.97 | Average = 33.43 |
|  | 33.76 | Std Dev = 0.41 |
|  | 33.56 | % CV = 1.22 |

Of the three regions, amplification of capsid was detected at the earliest and therefore was the most robust.

In additional experiments, reagents from Invitrogen Corporation (Carlsbad, Calif.) were used. In particular, these experiments used the Invitrogen SUPERSCRIPT III PLATINUM one-step quantitative RT-PCR system. The nucleic acid from Example 1(a) was suspended in 100 μl of reaction mix containing 2 μl of SUPERSCRIPT III PLATINUM Taq mix, 50 μl of 2× reaction mix, 4 mM MgSO$_4$, 2 μl of ROX, 1 pmol of amplification primers and 0.25 pmol of the probes. The suspended beads were transferred to a TAQMAN microtiter plate. The reaction conditions were 50° C. for 15 min for the RT reaction, followed by 95° C. for 2 min to denature the Taq polymerase antibody, followed by 50 cycles of alternating incubations at 95° C. for 15 seconds, and 60° C. for 1 min. Using the protocol of target capture primers and TAQMAN SUPERSCRIPT RT-PCR technology, 100% detection of 7.5 copies/ml (Cps/ml) of WNV RNA was observed (see, Table 2).

TABLE 2

Alternative NAT WNV assay

| WNV (copies/ml) | % Reactive |
| --- | --- |
| 30 | 100 |
| 15 | 100 |
| 7.5 | 100 |
| 0 | 0 |

N=12; A member of the BBI WNV RNA qualification panel QWN 702 (commercially available from BBI Diagnostics, Boston, Mass., see below) was diluted in defibrinated, delipidized human serum to required dilution.

EXAMPLE 4

Sensitivity of the Two-Probe Assay

The sensitivity of the two-probe assay using primer pairs VWNVA1 (SEQ ID NO:34) and VWNVA2 (SEQ ID NO:35) and the probes of SEQ ID NO:36 and SEQ ID NO:49, was tested. The probe of SEQ ID NO:36 is directed against the major U.S. WNV strain and the probe of SEQ ID NO:49 is directed against the major Ugandan strain. The internal control RNA of SEQ ID NO:17 (FIG. 2) and IC probe (SEQ ID NO:41) were also included. A 10,000 Cps/ml BBI panel member (commercially available from BBI Diagnostics, Boston, Mass.) was serially diluted for testing in triplicate as described above to establish the analytical sensitivity of the assay. In this assay, a reading of >45 Ct was considered negative. Results are shown in Table 3.

TABLE 3

| Target | BBI 702 Lineage 1-US | | BB1 701 Lineage 2-Ugandan | |
| --- | --- | --- | --- | --- |
| Cps/ml | Target Ct | IC Ct | Target Ct | IC Ct |
| 2500 | 34.5 | 43.1 | 34 | 44.6 |
| 1250 | 35.4 | 43.4 | 35.2 | 42.4 |
| 625 | 36.9 | 41.3 | 35.6 | 40.3 |
| 312 | 37.3 | 40.8 | 36.7 | 40.8 |
| 156 | 38.2 | 40.7 | 37.4 | 40.2 |
| 78 | 40.2 | 40 | 39.5 | 39.5 |
| 39 | 45 | 40 | 41.8 | 39.6 |
| 19 | 45.6 | 40 | 45.7 | 39.6 |
| 9 | 47.8 | 39 | 45 | 40.5 |
| Negative | 50 | 39 | 50 | 39.5 |

There was 100% positivity at 39 cps/ml for both lineages. The assay was highly sensitive and was capable of detecting 30 cps/ml.

EXAMPLE 5

Methods for Culturing and Inactivating WNV

Improved methods for preparing WNV in cell culture and heat inactivation procedures were developed. The inactivated virus can be used as a control in diagnostic and detection assays. For example, the viral RNA in cultured virus can be quantitated using established standards, and used in order to prepare standard curves for quantitative assays.

A. Infection of Vero Cells with WNV:

Vero cells (ATCC CCL-81) were grown in Eagle's Minimal Essential Medium (EMEM), 100 U Penicillin/ml, 100 μg/ml Streptomycin, 1 μg/ml Fungizone, supplemented with 10% fetal bovine serum (FBS) in 5% $CO_2$ at 37° C. A subconfluent Vero cell monolayer was infected with West Nile Virus strain 385–99 in a T75 flask. The cells were incubated for 1 hour at 37° C., in a humidified 5% $CO_2$ air mixture and the flask was shaken every 15 min. Then, maintenance medium (2% FBS, EMEM, Penicillin/Streptomycin/Amphotericin) was added and the cells were further incubated. Three days post-infection, a strong cytopathic effect was evident by rounding up of cells and cell death. The cell culture supernatant was collected, centrifuged for 15 min at 900×g at RT to remove cell debris, and the WNV suspension was frozen at −70° C.

B. Inactivation of WNV:

WNV suspension was heat-treated for 30 min at 56° C. or 65 min at 62.5–65° C., quenched for 15 min in an ice-water bath, centrifuged for 15 min at 900×g at 4° C. and stored at −70° C. The inactivation of WNV was controlled, and no further plaque formation in a plaque forming assay, as well as no infectivity of the WNV suspension on a Vero cell monolayer was observed.

C. Quantitation of Vero Cell-Cultured WNV

A seven member panel was prepared by serial dilution of the viral suspension of WNV propagated in Vero cells as described above. The copy number of each of these panel members was established using the WNV RNA Qualification Panel QWN702, commercially available from BBI Diagnostics, Boston, Mass. The panel consists of 15 members ranging from 10,000–30 copies/ml of Vero cell-cultured WNV. The panel members were assayed in triplicate to obtain a standard graph. Live samples, as well as samples inactivated as described above, were tested in triplicate and the results are shown in Table 4. The range represents the results from two versions of the standard graph obtained with BBI panel members. Results are also expressed as copies/pfu based on pfu determination which was $7.07 \times 10^7$ pfu/ml (1 pfu=~1000 copies).

TABLE 4

| Culture | Live WNV | | Heat Inactivated WNV | |
|---|---|---|---|---|
| Dilution | Cps/dilution | Cps/ml | Cps/dilution | cps/ml |
| Direct | Not Tested | Not Tested | Not Tested | Not Tested |
| $1 \times 10^{-4}$ | $0.52–1.1 \times 10^{7}$ | $0.52–1.1 \times 10^{11}$ | $1.6–3.0 \times 10^{6}$ | $1.6–3.0 \times 10^{10}$ |
| $1 \times 10^{-5}$ | $0.66–1.1 \times 10^{6}$ | $0.66–1.1 \times 10^{11}$ | $1.59–2.3 \times 10^{5}$ | $1.59–2.3 \times 10^{10}$ |
| $1 \times 10^{-6}$ | $0.70–1.0 \times 10^{5}$ | $0.70–1.0 \times 10^{11}$ | $1.88–2.1 \times 10^{4}$ | $1.88–2.3 \times 10^{10}$ |
| $1 \times 10^{-7}$ | $0.72–0.74 \times 10^{4}$ | $0.72–0.74 \times 10^{11}$ | $2.6–2.8 \times 10^{3}$ | $2.6–2.8 \times 10^{10}$ |
| $1 \times 10^{-8}$ | $0.87–1.0 \times 10^{3}$ | $0.87–1.0 \times 10^{11}$ | $4.1 \times 10^{2}$ | $4.1 \times 10^{10}$ |

Accordingly, novel WNV sequences and detection assays using these sequences have been disclosed. From the foregoing, it will be appreciated that, although specific embodiments of the invention have been described herein for purposes of illustration, various modifications may be made without deviating from the spirit and scope thereof.

The invention claimed is:

1. A method for detecting the presence of West Nile virus (WNV) in a biological sample, the method comprising:
   isolating nucleic acids from a biological sample suspected of containing WNV;
   amplifying the nucleic acids using a sense and an antisense primer wherein each of the primers is not more than about 60 nucleotides in length and is sufficiently complementary to a portion of the antisense and sense strands, respectively, of the isolated nucleic acid to hybridize therewith to allow amplification of said WNV nucleic acids, and
   (a) the sense primer comprises SEQ ID NO:34;
   (b) the antisense primer comprises SEQ ID NO:35; and
   detecting the presence of the amplified WNV nucleic acids as an indication of the presence of WNV in the sample.

2. The method of claim 1, wherein the nucleic acids are isolated from the biological sample by a method comprising:
   (a) contacting a solid support comprising capture nucleic acids associated therewith with a biological sample under hybridizing conditions wherein WNV nucleic acid strands, if present in the biological sample, hybridize with the capture nucleic acids; and
   (b) separating the solid support from the sample.

3. The method of claim 2, wherein the solid support comprises beads.

4. The method of claim 3, wherein the beads are magnetic beads.

5. The method of claim 4, wherein the isolating, amplifying and detecting are performed in a single container.

6. The method of claim 2, wherein the capture nucleic acids comprise one or more oligonucleotides, wherein each of the oligonucleotides is not more than about 60 nucleotides in length and comprises at least 10 contiguous nucleotides from a sequence selected from the group consisting of SEQ ID NOS:8 and 45, wherein the capture nucleic acids selectively bind to WNV nucleic acids from said biological sample.

7. The method of claim 6, wherein the capture nucleic acids further comprise a homopolymer chain of about 10–25 nucleotides in length, selected from the group consisting of polyA, polyT, polyG, polyC, and polyU.

8. The method of claim 7, wherein the homopolymer chain is a polyA chain.

9. The method of claim 1, wherein amplifying comprises RT-PCR, transcription-mediated amplification (TMA) or a fluorogenic 5' nuclease assay, or a combination thereof.

10. The method of claim 2, wherein amplifying comprises a fluorogenic 5' nuclease assay using the sense primer and the antisense primer and detecting is done using at least one probe comprising a detectable label.

11. The method of claim 10, wherein the at least one probe is not more than 60 nucleotides in length and comprises the sequence of SEQ ID NO:52 or the sequence of SEQ ID NO:53 when the sense primer comprises the sequence of SEQ ID NO:34, wherein the probe selectively binds to said WNV nucleic acids.

12. The method of claim 11, wherein the method comprises using a probe comprising the sequence of SEQ ID NO:52 and a probe comprising the sequence of SEQ ID NO:53 when the sense primer comprises the sequence of SEQ ID NO:34.

13. The method of either of claims 11 or 12, wherein the probe further comprises detectable labels at the 5'-end and at the 3'-end.

14. The method of claim 10, wherein the detectable label is a fluorescent label selected from the group consisting of 6-carboxyfluorescein (6-FAM), tetramethyl rhodamine (TAMRA), and 2', 4', 5', 7',-tetrachloro -4-7-dichlorofluorescein (TET).

15. The method of claim 1, wherein an internal control sequence is present.

16. The method of claim 15, wherein the internal control sequence comprises the nucleotide sequence of FIG. 2 (SEQ ID NO:17).

17. The method of claim 16, further comprising a detectably labeled probe sequence for the internal control sequence.

18. The method of claim 17, wherein the detectably labeled probe sequence for the internal control sequence comprises the sequence of SEQ ID NO:40.

* * * * *

SEQUENCE LISTING

<160> NUMBER OF SEQ ID NOS: 55

<210> SEQ ID NO 1
<211> LENGTH: 23
<212> TYPE: DNA
<213> ORGANISM: Artificial
<220> FEATURE:
<223> OTHER INFORMATION: oligonucleotide

<400> SEQUENCE: 1
gcacatgtat cccacatcca ttg                      23

<210> SEQ ID NO 2
<211> LENGTH: 23
<212> TYPE: DNA
<213> ORGANISM: Artificial
<220> FEATURE:
<223> OTHER INFORMATION: oligonucleotide

<400> SEQUENCE: 2
ctctgacaat gcataggttc ttt                      23

<210> SEQ ID NO 3
<211> LENGTH: 21
<212> TYPE: DNA
<213> ORGANISM: Artificial
<220> FEATURE:
<223> OTHER INFORMATION: oligonucleotide

<400> SEQUENCE: 3
ccagcagctg ttggaatcgt g                        21

<210> SEQ ID NO 4
<211> LENGTH: 22
<212> TYPE: DNA
<213> ORGANISM: Artificial
<220> FEATURE:
<223> OTHER INFORMATION: oligonucleotide

<400> SEQUENCE: 4
tgacatctgt gacgtcagta gc                       22

<210> SEQ ID NO 5
<211> LENGTH: 23
<212> TYPE: DNA
<213> ORGANISM: Artificial

```
<220> FEATURE:
<223> OTHER INFORMATION: oligonucleotide

<400> SEQUENCE: 5
tttaccgtca tcatcacctt ccc                                         23

<210> SEQ ID NO 6
<211> LENGTH: 23
<212> TYPE: DNA
<213> ORGANISM: Artificial
<220> FEATURE:
<223> OTHER INFORMATION: oligonucleotide

<400> SEQUENCE: 6
ttggaagtta gagagggtaa ctg                                         23

<210> SEQ ID NO 7
<211> LENGTH: 22
<212> TYPE: DNA
<213> ORGANISM: Artificial
<220> FEATURE:
<223> OTHER INFORMATION: oligonucleotide

<400> SEQUENCE: 7
ctcctacgct ggcgatcagg cc                                          22

<210> SEQ ID NO 8
<211> LENGTH: 23
<212> TYPE: DNA
<213> ORGANISM: Artificial
<220> FEATURE:
<223> OTHER INFORMATION: oligonucleotide

<400> SEQUENCE: 8
tcatgactgc aattccggtc ttt                                         23

<210> SEQ ID NO 9
<211> LENGTH: 21
<212> TYPE: DNA
<213> ORGANISM: Artificial
<220> FEATURE:
<223> OTHER INFORMATION: oligonucleotide

<400> SEQUENCE: 9
gagctccgcc gattgatagc a                                           21

<210> SEQ ID NO 10
<211> LENGTH: 21
<212> TYPE: DNA
<213> ORGANISM: Artificial
<220> FEATURE:
<223> OTHER INFORMATION: oligonucleotide

<400> SEQUENCE: 10
ctggtcaagg tccctagttc c                                           21

<210> SEQ ID NO 11
<211> LENGTH: 25
<212> TYPE: DNA
<213> ORGANISM: Artificial
<220> FEATURE:
<223> OTHER INFORMATION: oligonucleotide

<400> SEQUENCE: 11
ttcttaaaac tcagaaggtg tttca                                       25
```

```
<210> SEQ ID NO 12
<211> LENGTH: 24
<212> TYPE: DNA
<213> ORGANISM: Artificial
<220> FEATURE:
<223> OTHER INFORMATION: oligonucleotide

<400> SEQUENCE: 12
tcgctgtttg tttgttcaca cctc                                              24

<210> SEQ ID NO 13
<211> LENGTH: 26
<212> TYPE: DNA
<213> ORGANISM: Artificial
<220> FEATURE:
<223> OTHER INFORMATION: oligonucleotide

<400> SEQUENCE: 13
tccatcgatc cagcactgct cgggtc                                            26

<210> SEQ ID NO 14
<211> LENGTH: 23
<212> TYPE: DNA
<213> ORGANISM: Artificial
<220> FEATURE:
<223> OTHER INFORMATION: oligonucleotide

<400> SEQUENCE: 14
ggagcaattg ctgtgaacct gaa                                               23

<210> SEQ ID NO 15
<211> LENGTH: 21
<212> TYPE: DNA
<213> ORGANISM: Artificial
<220> FEATURE:
<223> OTHER INFORMATION: oligonucleotide

<400> SEQUENCE: 15
gaacgccaag agagccaaca c                                                 21

<210> SEQ ID NO 16
<211> LENGTH: 22
<212> TYPE: DNA
<213> ORGANISM: Artificial
<220> FEATURE:
<223> OTHER INFORMATION: oligonucleotide

<400> SEQUENCE: 16
tcgtattggc cccttgccgt cg                                                22

<210> SEQ ID NO 17
<211> LENGTH: 967
<212> TYPE: DNA
<213> ORGANISM: Artificial
<220> FEATURE:
<223> OTHER INFORMATION: West Nile Virus where bases 153-173 have been
      altered

<400> SEQUENCE: 17
agtagttcgc ctgtgtgagc tgacaaactt agtagtgttt gtgaggatta acaacaatta       60
acacagtgcg agctgtttct tagcacgaag atctcgatgt ctaagaaacc aggagggccc      120
ggcaagagcc gggctgtcaa tatgctaaaa cgcagtgaca tgcaggtcta gcttccttga      180
ttggactgaa gagggctatg ttgagcctga tcgacggcaa ggggccaata cgatttgtgt      240
tggctctctt ggcgttcttc aggttcacag caattgctcc gacccgagca gtgctggatc      300
```

-continued

| | |
|---|---|
| gatggagagg tgtgaacaaa caaacagcga tgaaacacct tctgagtttt aagaaggaac | 360 |
| tagggacctt gaccagtgct atcaatcggc ggagctcaaa acaaaagaaa agaggaggaa | 420 |
| agaccggaat tgcagtcatg attggcctga tcgccagcgt aggagcagtt accctctcta | 480 |
| acttccaagg gaaggtgatg atgacggtaa atgctactga cgtcacagat gtcatcacga | 540 |
| ttccaacagc tgctggaaag aacctatgca ttgtcagagc aatggatgtg ggatacatgt | 600 |
| gcgatgatac tatcacttat gaatgcccag tgctgtcggc tggtaatgat ccagaagaca | 660 |
| tcgactgttg gtgcacaaag tcagcagtct acgtcaggta tggaagatgc accaagacac | 720 |
| gccactcaag acgcagtcgg aggtcactga cagtgcagac acgcgagaa agcactctag | 780 |
| cgaacaagaa gggggcttgg atggacagca ccaaggccac aaggtatttg gtaaaaacag | 840 |
| aatcatggat cttgaggaac cctggatatg ccctggtggc agccgtcatt ggttggatgc | 900 |
| ttgggagcaa caccatgcag agagttgtgt ttgtcgtgct attgcttttg gtggccccag | 960 |
| cttacag | 967 |

<210> SEQ ID NO 18
<211> LENGTH: 44
<212> TYPE: DNA
<213> ORGANISM: Artificial
<220> FEATURE:
<223> OTHER INFORMATION: oligonucleotide

<400> SEQUENCE: 18

| | |
|---|---|
| aaaaaaaaaa aaaaaaaaaa agcacatgta tcccacatcc attg | 44 |

<210> SEQ ID NO 19
<211> LENGTH: 44
<212> TYPE: DNA
<213> ORGANISM: Artificial
<220> FEATURE:
<223> OTHER INFORMATION: oligonucleotide

<400> SEQUENCE: 19

| | |
|---|---|
| aaaaaaaaaa aaaaaaaaaa actctgacaa tgcataggtt cttt | 44 |

<210> SEQ ID NO 20
<211> LENGTH: 42
<212> TYPE: DNA
<213> ORGANISM: Artificial
<220> FEATURE:
<223> OTHER INFORMATION: oligonucleotide

<400> SEQUENCE: 20

| | |
|---|---|
| aaaaaaaaaa aaaaaaaaaa accagcagct gttggaatcg tg | 42 |

<210> SEQ ID NO 21
<211> LENGTH: 44
<212> TYPE: DNA
<213> ORGANISM: Artificial
<220> FEATURE:
<223> OTHER INFORMATION: oligonucleotide

<400> SEQUENCE: 21

| | |
|---|---|
| aaaaaaaaaa aaaaaaaaaa aatgacatct gtgacgtcag tagc | 44 |

<210> SEQ ID NO 22
<211> LENGTH: 45
<212> TYPE: DNA
<213> ORGANISM: Artificial
<220> FEATURE:
<223> OTHER INFORMATION: oligonucleotide

```
<400> SEQUENCE: 22
aaaaaaaaaa aaaaaaaaaa aatttaccgt catcatcacc ttccc              45

<210> SEQ ID NO 23
<211> LENGTH: 44
<212> TYPE: DNA
<213> ORGANISM: Artificial
<220> FEATURE:
<223> OTHER INFORMATION: oligonucleotide

<400> SEQUENCE: 23
aaaaaaaaaa aaaaaaaaaa attggaagtt agagagggta actg               44

<210> SEQ ID NO 24
<211> LENGTH: 43
<212> TYPE: DNA
<213> ORGANISM: Artificial
<220> FEATURE:
<223> OTHER INFORMATION: oligonucleotide

<400> SEQUENCE: 24
aaaaaaaaaa aaaaaaaaaa actcctacgc tggcgatcag gcc                43

<210> SEQ ID NO 25
<211> LENGTH: 46
<212> TYPE: DNA
<213> ORGANISM: Artificial
<220> FEATURE:
<223> OTHER INFORMATION: oligonucleotide

<400> SEQUENCE: 25
aaaaaaaaaa aaaaaaaaaa aaatcatgac tgcaattccg gtcttt             46

<210> SEQ ID NO 26
<211> LENGTH: 42
<212> TYPE: DNA
<213> ORGANISM: Artificial
<220> FEATURE:
<223> OTHER INFORMATION: oligonucleotide

<400> SEQUENCE: 26
aaaaaaaaaa aaaaaaaaaa agagctccgc cgattgatag ca                 42

<210> SEQ ID NO 27
<211> LENGTH: 42
<212> TYPE: DNA
<213> ORGANISM: Artificial
<220> FEATURE:
<223> OTHER INFORMATION: oligonucleotide

<400> SEQUENCE: 27
aaaaaaaaaa aaaaaaaaaa actggtcaag gtccctagtt cc                 42

<210> SEQ ID NO 28
<211> LENGTH: 46
<212> TYPE: DNA
<213> ORGANISM: Artificial
<220> FEATURE:
<223> OTHER INFORMATION: oligonucleotide

<400> SEQUENCE: 28
aaaaaaaaaa aaaaaaaaaa attcttaaaa ctcagaaggt gtttca             46
```

<210> SEQ ID NO 29
<211> LENGTH: 45
<212> TYPE: DNA
<213> ORGANISM: Artificial
<220> FEATURE:
<223> OTHER INFORMATION: oligonucleotide

<400> SEQUENCE: 29
aaaaaaaaaa aaaaaaaaaa atcgctgttt gtttgttcac acctc            45

<210> SEQ ID NO 30
<211> LENGTH: 47
<212> TYPE: DNA
<213> ORGANISM: Artificial
<220> FEATURE:
<223> OTHER INFORMATION: oligonucleotide

<400> SEQUENCE: 30
aaaaaaaaaa aaaaaaaaaa atccatcgat ccagcactgc tcgggtc          47

<210> SEQ ID NO 31
<211> LENGTH: 44
<212> TYPE: DNA
<213> ORGANISM: Artificial
<220> FEATURE:
<223> OTHER INFORMATION: oligonucleotide

<400> SEQUENCE: 31
aaaaaaaaaa aaaaaaaaaa aggagcaatt gctgtgaacc tgaa             44

<210> SEQ ID NO 32
<211> LENGTH: 42
<212> TYPE: DNA
<213> ORGANISM: Artificial
<220> FEATURE:
<223> OTHER INFORMATION: oligonucleotide

<400> SEQUENCE: 32
aaaaaaaaaa aaaaaaaaaa agaacgccaa gagagccaac ac               42

<210> SEQ ID NO 33
<211> LENGTH: 46
<212> TYPE: DNA
<213> ORGANISM: Artificial
<220> FEATURE:
<223> OTHER INFORMATION: oligonucleotide

<400> SEQUENCE: 33
aaaaaaaaaa aaaaaaaaaa aaaatcgtat tggccccttg ccgtcg           46

<210> SEQ ID NO 34
<211> LENGTH: 21
<212> TYPE: DNA
<213> ORGANISM: Artificial
<220> FEATURE:
<223> OTHER INFORMATION: oligonucleotide

<400> SEQUENCE: 34
ccgggctgtc aatatgctaa a                                      21

<210> SEQ ID NO 35
<211> LENGTH: 22
<212> TYPE: DNA
<213> ORGANISM: Artificial
<220> FEATURE:
<223> OTHER INFORMATION: oligonucleotide

```
<400> SEQUENCE: 35
agccctcttc agtccaatca ag                                    22

<210> SEQ ID NO 36
<211> LENGTH: 19
<212> TYPE: DNA
<213> ORGANISM: Artificial
<220> FEATURE:
<223> OTHER INFORMATION: oligonucleotide

<400> SEQUENCE: 36
cggaatgccc cgcgtgttg                                        19

<210> SEQ ID NO 37
<211> LENGTH: 17
<212> TYPE: DNA
<213> ORGANISM: Artificial
<220> FEATURE:
<223> OTHER INFORMATION: oligonucleotide

<400> SEQUENCE: 37
cagaccacgc tacggcg                                          17

<210> SEQ ID NO 38
<211> LENGTH: 15
<212> TYPE: DNA
<213> ORGANISM: Artificial
<220> FEATURE:
<223> OTHER INFORMATION: oligonucleotide

<400> SEQUENCE: 38
ctagggccgc gtggg                                            15

<210> SEQ ID NO 39
<211> LENGTH: 24
<212> TYPE: DNA
<213> ORGANISM: Artificial
<220> FEATURE:
<223> OTHER INFORMATION: oligonucleotide

<400> SEQUENCE: 39
tctgcggaga gtgcagtctg cgat                                  24

<210> SEQ ID NO 40
<211> LENGTH: 21
<212> TYPE: DNA
<213> ORGANISM: Artificial
<220> FEATURE:
<223> OTHER INFORMATION: oligonucleotide

<400> SEQUENCE: 40
cagtgacatg caggtctagc t                                     21

<210> SEQ ID NO 41
<211> LENGTH: 23
<212> TYPE: DNA
<213> ORGANISM: Artificial
<220> FEATURE:
<223> OTHER INFORMATION: oligonucleotide

<400> SEQUENCE: 41
cccagtgaca tgcaggtcta gct                                   23
```

<210> SEQ ID NO 42
<211> LENGTH: 21
<212> TYPE: DNA
<213> ORGANISM: Artificial
<220> FEATURE:
<223> OTHER INFORMATION: oligonucleotide

<400> SEQUENCE: 42
tctgctcttc ctctccgtga a                                        21

<210> SEQ ID NO 43
<211> LENGTH: 21
<212> TYPE: DNA
<213> ORGANISM: Artificial
<220> FEATURE:
<223> OTHER INFORMATION: oligonucleotide

<400> SEQUENCE: 43
ctcttgccgg ctgatgtcta t                                        21

<210> SEQ ID NO 44
<211> LENGTH: 22
<212> TYPE: DNA
<213> ORGANISM: Artificial
<220> FEATURE:
<223> OTHER INFORMATION: oligonucleotide

<400> SEQUENCE: 44
tgcacgctga cactgggtgt gc                                       22

<210> SEQ ID NO 45
<211> LENGTH: 20
<212> TYPE: DNA
<213> ORGANISM: artificial
<220> FEATURE:
<223> OTHER INFORMATION: oligonucleotide

<400> SEQUENCE: 45
gtccacctct tgcgaaggac                                          20

<210> SEQ ID NO 46
<211> LENGTH: 21
<212> TYPE: DNA
<213> ORGANISM: artificial
<220> FEATURE:
<223> OTHER INFORMATION: oligonucleotide

<400> SEQUENCE: 46
ctgtgccgtg tggctggttg t                                        21

<210> SEQ ID NO 47
<211> LENGTH: 32
<212> TYPE: DNA
<213> ORGANISM: artificial
<220> FEATURE:
<223> OTHER INFORMATION: oligonucleotide

<400> SEQUENCE: 47
gtccacctct tgcgaaggac aaaaaaaaaa aa                            32

<210> SEQ ID NO 48
<211> LENGTH: 33
<212> TYPE: DNA
<213> ORGANISM: artificial
<220> FEATURE:
<223> OTHER INFORMATION: oligonucleotide

```
<400> SEQUENCE: 48
ctgtgccgtg tggctggttg taaaaaaaaa aaa                          33

<210> SEQ ID NO 49
<211> LENGTH: 19
<212> TYPE: DNA
<213> ORGANISM: artificial
<220> FEATURE:
<223> OTHER INFORMATION: oligonucleotide

<400> SEQUENCE: 49
cggtatgccc cgcggattg                                          19

<210> SEQ ID NO 50
<211> LENGTH: 20
<212> TYPE: DNA
<213> ORGANISM: artificial
<220> FEATURE:
<223> OTHER INFORMATION: oligonucleotide

<400> SEQUENCE: 50
cctagtctat cccaggtgtc                                         20

<210> SEQ ID NO 51
<211> LENGTH: 42
<212> TYPE: DNA
<213> ORGANISM: artificial
<220> FEATURE:
<223> OTHER INFORMATION: oligonucleotide

<400> SEQUENCE: 51
cctagtctat cccaggtgtc aaaaaaaaaa aaaaaaaaaa aa                42

<210> SEQ ID NO 52
<211> LENGTH: 19
<212> TYPE: DNA
<213> ORGANISM: artificial
<220> FEATURE:
<223> OTHER INFORMATION: oligonucleotide

<400> SEQUENCE: 52
cggaatgccc cgcgtgttg                                          19

<210> SEQ ID NO 53
<211> LENGTH: 19
<212> TYPE: DNA
<213> ORGANISM: artificial
<220> FEATURE:
<223> OTHER INFORMATION: oligonucleotide

<400> SEQUENCE: 53
cggtatgccc cgcggattg                                          19

<210> SEQ ID NO 54
<211> LENGTH: 24
<212> TYPE: DNA
<213> ORGANISM: artificial
<220> FEATURE:
<223> OTHER INFORMATION: oligonucleotide

<400> SEQUENCE: 54
tctgcggaga gtgcagtctg cgat                                    24
```

```
<210> SEQ ID NO 55
<211> LENGTH: 22
<212> TYPE: DNA
<213> ORGANISM: artificial
<220> FEATURE:
<223> OTHER INFORMATION: oligonucleotide

<400> SEQUENCE: 55
tgcacgctga cactgggtgt gc                                              22
```